(12) United States Patent
Alkhatib

(10) Patent No.: US 12,350,152 B2
(45) Date of Patent: Jul. 8, 2025

(54) DELIVERY AND RETRIEVAL SYSTEMS FOR COLLAPSIBLE/EXPANDABLE PROSTHETIC HEART VALVES

(71) Applicant: St. Jude Medical, LLC, Abbott Park, IL (US)

(72) Inventor: Yousef F. Alkhatib, Edina, MN (US)

(73) Assignee: St. Juse Medical, LLC, Abbott Park, IL (US)

( * ) Notice: Subject to any disclaimer, the term of this patent is extended or adjusted under 35 U.S.C. 154(b) by 493 days.

(21) Appl. No.: 17/740,894

(22) Filed: May 10, 2022

(65) Prior Publication Data

US 2022/0265425 A1 Aug. 25, 2022

Related U.S. Application Data

(60) Division of application No. 16/359,148, filed on Mar. 20, 2019, now Pat. No. 11,452,600, which is a
(Continued)

(51) Int. Cl.
*A61F 2/24* (2006.01)
*A61F 2/95* (2013.01)

(52) U.S. Cl.
CPC .......... *A61F 2/2436* (2013.01); *A61F 2/2439* (2013.01); *A61F 2/2427* (2013.01); *A61F 2002/9511* (2013.01)

(58) Field of Classification Search
CPC ...... A61F 2/2427; A61F 2/2436; A61F 2/243; A61F 2/2433; A61F 2/2439; A61F 2/95;
(Continued)

(56) References Cited

U.S. PATENT DOCUMENTS

| 4,423,730 A | 1/1984 | Gabbay |
| 5,078,720 A | 1/1992 | Burton et al. |

(Continued)

FOREIGN PATENT DOCUMENTS

| EP | 1129744 A1 | 9/2001 |
| EP | 1157673 A2 | 11/2001 |

(Continued)

OTHER PUBLICATIONS

International Search Report for Application No. PCT/US2009/000104 dated May 28, 2009.
(Continued)

*Primary Examiner* — Dianne Dornbusch
(74) *Attorney, Agent, or Firm* — SLEMAN & LUND LLP

(57) ABSTRACT

A system for delivering a collapsible and re-expandable prosthetic heart valve into a patient includes a valve support structure around which the valve is disposed in a collapsed condition. A sheath structure surrounds the collapsed valve, but can be moved relative to the valve to uncover it for expansion at the desired implant site in the patient. The sheath structure may be variously mounted and moved to deploy the valve in various ways. For example, the sheath structure may include multiple parts, each of which can be moved separately to separately deploy various parts of the valve. The apparatus may have other aspects, such as the ability to reverse deployment of the valve, the ability to pass other instrumentation through the valve delivery apparatus, the ability to be smoothly withdrawn from the patient after deployment of the valve, etc.

17 Claims, 28 Drawing Sheets

Related U.S. Application Data continuation of application No. 14/845,843, filed on Sep. 4, 2015, now Pat. No. 10,258,469, which is a division of application No. 12/735,273, filed as application No. PCT/US2009/000104 on Jan. 8, 2009, now Pat. No. 9,180,004.

(60) Provisional application No. 61/011,393, filed on Jan. 16, 2008.

(58) Field of Classification Search
CPC .. A61F 2/966; A61F 2/97; A61F 2/962; A61F 2002/9505; A61F 2002/9665
See application file for complete search history.

(56) References Cited

U.S. PATENT DOCUMENTS

| | | | |
|---|---|---|---|
| 5,158,548 A | 10/1992 | Lau et al. | |
| 5,201,757 A | 4/1993 | Heyn et al. | |
| 5,445,646 A | 8/1995 | Euteneuer et al. | |
| 5,484,444 A | 1/1996 | Braunschweiler et al. | |
| 5,693,083 A | 12/1997 | Baker et al. | |
| 5,702,418 A | 12/1997 | Ravenscroft | |
| 5,824,041 A | 10/1998 | Lenker et al. | |
| 5,924,424 A | 7/1999 | Stevens et al. | |
| 5,968,068 A | 10/1999 | Dehdashtian et al. | |
| 5,972,030 A | 10/1999 | Garrison et al. | |
| 5,980,533 A | 11/1999 | Holman | |
| 5,989,280 A | 11/1999 | Euteneuer et al. | |
| 6,019,790 A | 2/2000 | Holmberg et al. | |
| 6,068,634 A | 5/2000 | Lorentzen Cornelius et al. | |
| 6,102,942 A | 8/2000 | Ahari | |
| 6,139,572 A | 10/2000 | Campbell et al. | |
| 6,269,819 B1 | 8/2001 | Oz et al. | |
| 6,290,710 B1 | 9/2001 | Cryer et al. | |
| 6,306,141 B1 | 10/2001 | Jervis | |
| 6,391,050 B1 | 5/2002 | Broome | |
| 6,468,299 B2 | 10/2002 | Stack et al. | |
| 6,530,952 B2 | 3/2003 | Vesely | |
| 6,565,595 B1 | 5/2003 | DiCaprio et al. | |
| 6,579,305 B1 | 6/2003 | Lashinski | |
| 6,623,518 B2 | 9/2003 | Thompson et al. | |
| 6,858,034 B1 | 2/2005 | Hijlkema et al. | |
| 7,004,964 B2 | 2/2006 | Thompson et al. | |
| 7,011,681 B2 | 3/2006 | Vesely | |
| 7,235,095 B2 | 6/2007 | Haverkost et al. | |
| 7,473,271 B2 * | 1/2009 | Gunderson | A61F 2/95 623/1.12 |
| 7,553,324 B2 | 6/2009 | Andreas et al. | |
| 7,651,519 B2 | 1/2010 | Dittman | |
| 7,780,723 B2 | 8/2010 | Taylor | |
| 8,062,345 B2 | 11/2011 | Ouellette et al. | |
| 8,062,349 B2 | 11/2011 | Moore et al. | |
| 8,070,790 B2 | 12/2011 | Berra et al. | |
| 8,303,652 B2 | 11/2012 | Bokros et al. | |
| 8,403,977 B2 | 3/2013 | Case et al. | |
| 8,518,098 B2 | 8/2013 | Roeder et al. | |
| 8,679,174 B2 | 3/2014 | Ottma et al. | |
| 8,747,459 B2 | 6/2014 | Nguyen et al. | |
| 9,138,315 B2 | 9/2015 | Straubinger et al. | |
| 9,532,868 B2 | 1/2017 | Braido | |
| 2001/0002445 A1 | 5/2001 | Vesely | |
| 2001/0039450 A1 | 11/2001 | Pavcnik et al. | |
| 2002/0058994 A1 | 5/2002 | Hill et al. | |
| 2002/0103525 A1 | 8/2002 | Cummings | |
| 2002/0188341 A1 | 12/2002 | Elliott | |
| 2003/0033000 A1 | 2/2003 | DiCaprio et al. | |
| 2003/0163155 A1 | 8/2003 | Haverkost et al. | |
| 2003/0167060 A1 | 9/2003 | Buzzard et al. | |
| 2005/0033402 A1 | 2/2005 | Cully et al. | |
| 2005/0043790 A1 | 2/2005 | Seguin | |
| 2005/0203615 A1 | 9/2005 | Forster et al. | |
| 2006/0025844 A1 | 2/2006 | Majercak et al. | |
| 2006/0106415 A1 | 5/2006 | Gabbay | |
| 2006/0116572 A1 | 6/2006 | Case | |
| 2006/0142848 A1 | 6/2006 | Gabbay | |
| 2006/0155363 A1 | 7/2006 | LaDuca et al. | |
| 2006/0167468 A1 | 7/2006 | Gabbay | |
| 2006/0188408 A1 * | 8/2006 | Arbefeuille | A61F 2/95 623/1.11 |
| 2006/0200221 A1 | 9/2006 | Malewicz | |
| 2006/0217802 A1 | 9/2006 | Ruiz et al. | |
| 2007/0032850 A1 | 2/2007 | Ruiz et al. | |
| 2007/0073387 A1 | 3/2007 | Forster et al. | |
| 2007/0073391 A1 | 3/2007 | Bourang et al. | |
| 2007/0088431 A1 | 4/2007 | Bourang et al. | |
| 2007/0100435 A1 | 5/2007 | Case et al. | |
| 2007/0112422 A1 | 5/2007 | Dehdashtian | |
| 2007/0162100 A1 | 7/2007 | Gabbay | |
| 2007/0162103 A1 | 7/2007 | Case et al. | |
| 2007/0167955 A1 | 7/2007 | Arnault De La Menardiere et al. | |
| 2007/0168013 A1 | 7/2007 | Douglas | |
| 2007/0203561 A1 | 8/2007 | Forster et al. | |
| 2007/0203575 A1 | 8/2007 | Forster et al. | |
| 2007/0219629 A1 | 9/2007 | Bokros et al. | |
| 2007/0233222 A1 | 10/2007 | Roeder et al. | |
| 2007/0239271 A1 | 10/2007 | Nguyen | |
| 2007/0244546 A1 | 10/2007 | Francis | |
| 2007/0250151 A1 * | 10/2007 | Pereira | A61F 2/95 623/1.12 |
| 2008/0065011 A1 | 3/2008 | Marchand et al. | |
| 2008/0071367 A1 | 3/2008 | Bergin et al. | |
| 2008/0114435 A1 | 5/2008 | Bowe | |
| 2008/0140189 A1 | 6/2008 | Nguyen et al. | |
| 2008/0147182 A1 | 6/2008 | Righini et al. | |
| 2008/0262590 A1 * | 10/2008 | Murray | A61F 2/95 623/1.11 |
| 2009/0054975 A1 | 2/2009 | del Nido et al. | |
| 2009/0054976 A1 | 2/2009 | Tuval et al. | |
| 2009/0069890 A1 | 3/2009 | Suri et al. | |
| 2009/0099637 A1 | 4/2009 | Barthold et al. | |
| 2009/0264978 A1 | 10/2009 | Dieck et al. | |
| 2009/0281619 A1 | 11/2009 | Le et al. | |
| 2010/0256751 A1 | 10/2010 | Rowe et al. | |
| 2010/0286768 A1 | 11/2010 | Alkhatib | |
| 2011/0224678 A1 | 9/2011 | Gabbay | |
| 2011/0307049 A1 | 12/2011 | Kao | |

FOREIGN PATENT DOCUMENTS

| | | |
|---|---|---|
| WO | 03071988 A1 | 9/2003 |
| WO | 2004039242 A2 | 5/2004 |
| WO | 2005062980 A2 | 7/2005 |
| WO | 2007016187 A2 | 2/2007 |
| WO | 2007059293 A1 | 5/2007 |
| WO | 2007098232 A2 | 8/2007 |
| WO | 2008029296 A2 | 3/2008 |
| WO | 2008138584 A1 | 11/2008 |
| WO | 2009002548 A1 | 12/2008 |
| WO | 2009091509 A1 | 7/2009 |
| WO | 10051025 A1 | 5/2010 |
| WO | 10087975 A1 | 8/2010 |

OTHER PUBLICATIONS

Cribier, Alain G. "The Odyssey of TAVR from concept to clinical reality." Texas Heart Institute journal vol. 41,2125-30. Apr. 1, 2014, doi:10.14503/THIJ-14-4137.

Cribier, Alain. "The development of transcatheter aortic valve replacement (TAVR)." Global cardiology science & practice vol. 2016,4 e201632. Dec. 30, 2016, 15 pages, doi: 1 0.21542/gcsp.2016.32.

Tables of contents from textbook entitled "Interventionelle Kardiologie, Angiologie und Kardiovaskularchirurgie" (Engl.: interventional cardiology, angiology and cardiovascular surgery), Hom bach (Hrdg.), published by Schattauer, 2001, 11 pages.

Tables of contents from textbook entitled "Textbook of Interventional Cardiology- Fourth Edition", published by Saunders, 2003, 5 pages.

Excerpt from textbook entitled "Textbook of Interventional Cardiology- Fourth Edition", published by Saunders, 2003, concerning transcatheter cardiac stent valves, 5 pages.

(56) References Cited

OTHER PUBLICATIONS

Tables of contents and excerpts from textbook entitled "Oxford Textbook of Interventional Cardiology", published by Oxford University Press, 2010, 21 pages.
Excerpts taken from the textbook: "Textbook of Interventional Cardiology, Fifth Edition", Topol, published by Saunders, 2008, 21 pages.
Excerpts taken from the textbook: Transcatheter Valve Repair, Hijazi et al., published by Taylor & Francis, 2006, 11 ages.

* cited by examiner

DELIVERY AND RETRIEVAL SYSTEMS FOR COLLAPSIBLE/EXPANDABLE PROSTHETIC HEART VALVES

CROSS-REFERENCE TO RELATED APPLICATIONS

The present application is a divisional of U.S. patent application Ser. No. 16/359,148, filed Mar. 20, 2019, now U.S. Pat. No. 11,452,600, which is a continuation of U.S. patent application Ser. No. 14/845,843, filed Sep. 4, 2015, now U.S. Pat. No. 10,258,469, which is a divisional of U.S. patent application Ser. No. 12/735,273, filed Jun. 28, 2010, now U.S. Pat. No. 9,180,04, which application is a national phase entry under 35 U.S.C. § 371 of International Application No. PCT/US2009/000104, filed Jan. 8, 2009, which claims the benefit of the filing date of U.S. Provisional Patent Application No. 61/011,393 filed Jan. 16, 2008, the disclosures of all of which are hereby incorporated herein by reference.

BACKGROUND OF THE INVENTION

This invention relates to prosthetic heart valves. More particularly, the invention relates to prosthetic heart valves that can be collapsed to a relatively small circumferential size for delivery into a patient's body with reduced invasiveness to the patient, and which can then be re-expanded to operating size at the intended implant site in the patient. Still more particularly, the invention relates to methods and apparatus for delivering a valve of the type described above into a patient and re-expanding the valve at the implant site. Another possible aspect of the invention relates to methods and apparatus for repositioning the valve in the patient and/or for retrieving the valve from the patient if desired.

SUMMARY OF THE INVENTION

In accordance with certain possible aspects of the invention, apparatus for delivering a collapsible and re-expandable prosthetic heart valve to an implant site in a patient may include a valve support structure around which the valve is disposed in a collapsed condition. A sheath structure may surround the valve on the valve support structure. The apparatus may still further include means for moving the sheath structure relative to the valve support structure to uncover the valve for expansion at the implant site. The valve may have first and second surface portions that face in respective opposite first and second directions along an axis around which the valve is disposed on the valve support structure, and the valve support structure may have third and fourth surface portions that respectively face in the second and first directions. The first and third surface portions may be positioned adjacent to and facing one another, and the second and fourth surface portions may be positioned adjacent to and facing one another to substantially prevent relative movement of the valve and the valve support structure along said axis while the valve is disposed around the valve support structure in the collapsed condition.

In accordance with a further possible aspect of the invention, the sheath structure may include a first sheath part that covers a first axial end part of the valve in the collapsed condition, and a second sheath part that covers a second axial end part of the valve in the collapsed condition. In such a case, the means for moving may make possible movement of one of the sheath parts relative to the other sheath part. Further in such a case, the means for moving may include first means for moving the first sheath part in a first direction that is away from the second axial end part of the valve; and the means for moving may further include second means for moving the second sheath part in a second direction that is away from the first axial end part of the valve. If provided, the first and second sheath parts may partly overlap one another.

In accordance with another possible aspect of the invention, the valve support structure may be configured to substantially prevent the valve from rotating about the valve support structure.

In accordance with still another possible aspect of the invention, the apparatus may further include means for drawing a portion of the valve that has been uncovered by the sheath structure radially inwardly toward the valve support structure.

In accordance with yet another possible aspect of the invention, the means for moving may additionally allow the sheath structure to be again moved relative to the valve support structure after expansion of the valve so that the sheath structure covers the valve support structure.

In accordance with still another possible aspect of the invention, the valve support structure may define a passageway that extends from a first location that is proximal of the valve to a second location that is distal of the valve, with the first location being closer to an operator of the apparatus than the second location.

In accordance with yet another possible aspect of the invention, the valve support structure may define a passageway for fluid communication from a location that is proximal of the valve to the valve, with said location being closer to an operator of the apparatus than the valve.

In a case in which the valve has first and second axial end parts, as mentioned above, one of the axial end parts may include valve leaflets, and the other axial end part may include valve frame structure without leaflets.

In accordance with another possible aspect of the invention, the apparatus may include a distal tip structure secured to a portion of the sheath structure that is most distant from an operator of the apparatus. The distal tip structure may have a vent from inside the sheath structure to outside the apparatus for facilitating de-airing of an interior of the sheath structure.

In accordance with still another possible aspect of the invention, the apparatus may include a distal tip structure secured to a portion of the sheath structure that is most distant from an operator of the apparatus, and a shaft for allowing the distal tip structure and said portion of the sheath structure to be moved distally away from the valve support. The shaft may include an articulation proximal to said portion of the sheath structure.

In accordance with certain other possible aspects of the invention, apparatus for delivering a collapsible and re-expandable prosthetic heart valve to an implant site in a patient may include a valve support structure around which the valve is disposed in a collapsed condition, the valve support structure having axially spaced proximal and distal portions, with the proximal portion being closer than the distal portion to an operator of the apparatus. The apparatus may further include a sheath structure surrounding the valve on the valve support structure. The apparatus may still further include means for moving the sheath structure in a distal direction relative to the valve support structure to uncover the valve for expansion at the implant site.

In a case such as is mentioned in the preceding paragraph, the apparatus may further include a second sheath structure surrounding the sheath structure, and second means for moving the second sheath structure in a proximal direction relative to the valve support structure to uncover the sheath structure.

Further in a case such as is mentioned two paragraphs above, the valve support structure may include elements that extend radially outwardly into a tubular geometric shape in which a frame structure of the collapsed valve is disposed, said elements being positioned to interfere with motion of the valve (parallel to a longitudinal axis of the tubular geometric shape) relative to the valve support structure.

Still further in a case such as is mentioned three paragraphs above, the means for moving may comprise an articulation proximal of the sheath structure but distal of the valve support structure when the means for moving has moved the sheath structure to completely uncover the valve.

Further in a case such as is mentioned four paragraphs above, the apparatus may further include a distal tip structure secured to a distal end of the sheath structure, the distal tip structure defining a vent from inside the sheath structure to outside of the apparatus.

In accordance with certain still other possible aspects of the invention, a method of operating apparatus for delivering a collapsible and re-expandable prosthetic heart valve to an implant site in a patient may include introducing the apparatus into the patient with the valve disposed in a collapsed condition around a valve support structure, and with a sheath structure surrounding the valve. The method may further include moving the sheath structure relative to the valve support structure to uncover the valve for expansion at the implant site.

In accordance with a further possible aspect of the invention, the method may include moving the sheath structure relative to the valve support structure after expansion of the valve so that the sheath structure covers the valve support structure. The method may then further include withdrawing the apparatus from the patient.

In accordance with still another possible aspect of the invention, the valve may be at a first location in the apparatus that is remote from an operator the apparatus, and the moving may move the sheath structure to a second location that is more remote from the operator than the first location. In such a case, during the introducing the sheath structure may be covered by a second sheath structure, and the method may further include, prior to the moving, moving the second sheath structure to a third location that is closer to the operator than the first location.

In accordance with yet another possible aspect of the invention, the method may further include passing additional instrumentation through the valve support structure to a location in the patient that is more remote from an operator of the apparatus than the valve support structure.

In accordance with still another possible aspect of the invention, the method may further include passing fluid through a portion of the valve support structure from a location (which is closer to an operator of the apparatus than the valve support structure) to the valve.

In accordance with yet another possible aspect of the invention, the method may further include drawing a portion of the valve radially inwardly toward the valve support structure after the moving has uncovered that portion of the valve.

Further features of the invention, its nature and various advantages, will be more apparent from the accompanying drawings and the following detailed description.

DETAILED DESCRIPTION

Figure 1:
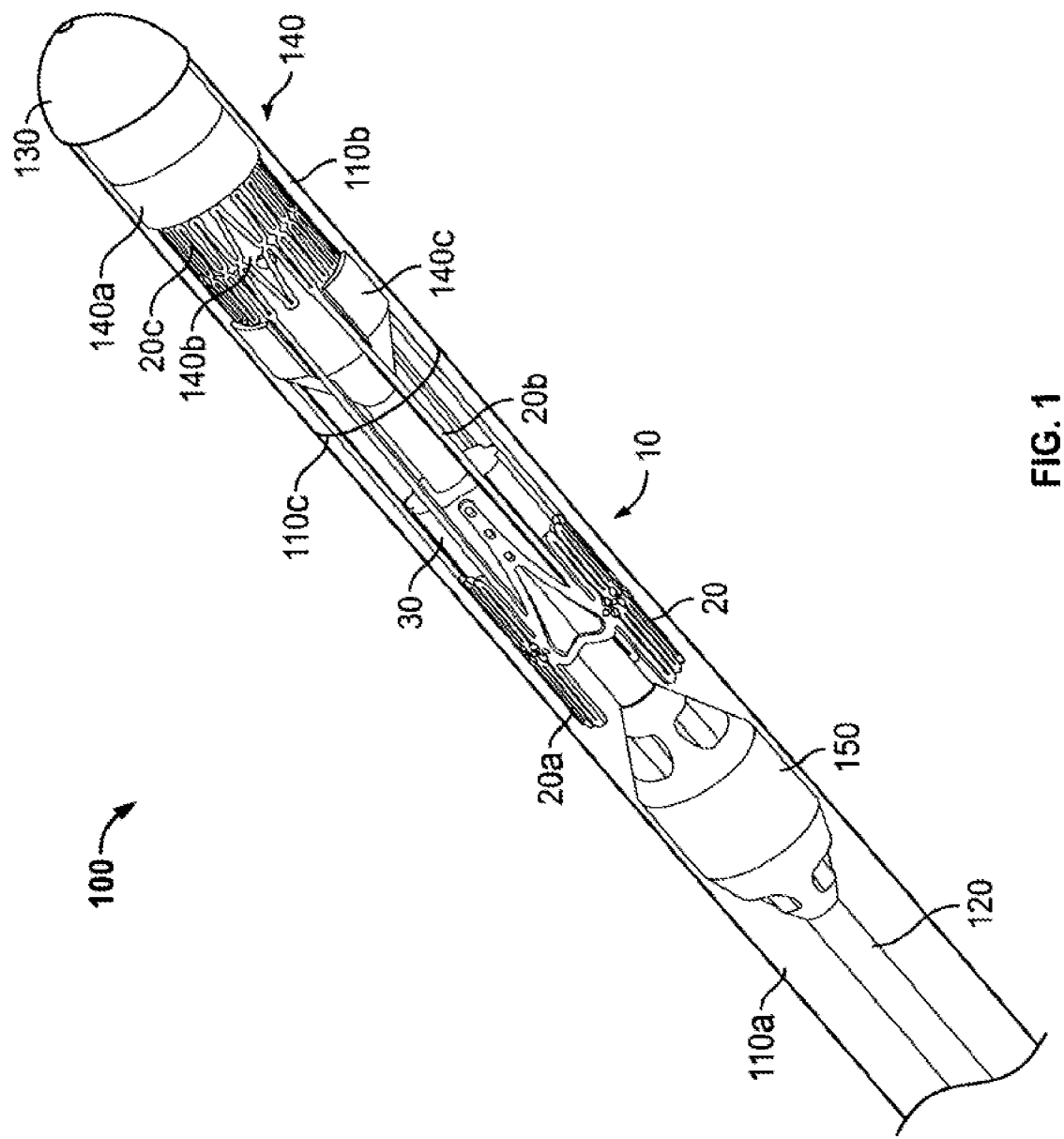
FIG. 1 is a simplified isometric or perspective view of an illustrative embodiment of portions of apparatus in accordance with the invention.

Examples of valves with which the present invention can be used are shown in Braido U.S. patent application Ser. No. 11/906,133, filed Sep. 28, 2007, which is hereby incorporated by reference herein in its entirety. Such valves typically include a relatively stiff frame (e.g., of metal or other appropriate material(s)) and flexible leaflets (e.g., of tissue or other appropriate material(s)) that are attached to the frame. Such valves may also include other components, such as layers of additional tissue (e.g., for buffering) and layers of fabric (e.g., to promote tissue in-growth). The FIGS. that form part of the present disclosure tend to concentrate on the frame of the depicted valves, and to omit or greatly simplify other valve components such as the leaflets, other layers of tissue and/or fabric, sutures, etc. This is done to simplify the FIGS. and to reduce the degree to which the valve obscures features of the present structures. It should be understood, however, that wherever a valve frame is shown herein, all other components of a complete prosthetic valve are also present with the frame, although those other components are not depicted (either at all or in full detail) for the reasons mentioned above.

The present invention will be shown and described herein primarily in the context of prosthetic aortic valves. It will be understood that the invention can also be applied to prostheses for other valves in the heart. The invention will sometimes be referred to herein in the context of introducing a replacement (prosthetic) aortic valve into a patient's heart via the left ventricle at the apex (lower extremity) of the patient's heart. From such an apical access point, the valve is moved upward to the vicinity of the annulus of the patient's native aortic valve, where the replacement heart valve is released from the delivery apparatus and thereby implanted in the patient. (The word "upward" and other similar terms are used as though the patient were standing, although the patient will of course not be standing during a heart valve replacement procedure.) It will be understood that this (exemplary) implant site can be approached in other ways (e.g., percutaneous transluminal, transaortic, transfemoral, or using any incision along the length of the ascending or descending aorta).

The delivery apparatus and methods of this invention may allow the prosthetic heart valve to be delivered and released in different ways. For example, a construction of the delivery apparatus may allow different parts of the replacement heart valve to be released before other parts are released, and the delivery apparatus may allow the order in which different parts of the valve are released to be varied in different situations. In all cases the word proximal is used to refer to the part of the valve or the part of the valve delivery apparatus that is closer to the operator (medical practitioner) of the apparatus. The word distal is used to refer to the part of valve or apparatus that is farther from the operator. The delivery apparatus may allow the distal part of the valve to be released from that apparatus before or after the proximal part of the valve is released. Also, the orientation of the valve in the delivery apparatus may be different in different situations. In some cases the part of the valve that will be upstream in the patient's blood flow when the valve is implanted may be located proximally in the delivery apparatus. In other cases the part of the valve that will be downstream in the patient's blood flow when the valve is implanted may be located proximally in the delivery apparatus. Various combinations of the foregoing options are possible, so that, for example, the portion of the valve that is released from the delivery apparatus first may be (1) proximal and downstream, (2) distal and downstream, (3) proximal and upstream, or (4) distal and upstream.

FIG. 1 shows an illustrative embodiment of the distal portion of prosthetic valve delivery apparatus 100 in accordance with the invention. FIG. 1 shows apparatus 100 containing a prosthetic aortic heart valve 10 prior to deployment of that valve. Valve 10 is visible in apparatus 100 because an outer, hollow, tubular sheath 110a-b of apparatus 100 is shown as though substantially transparent, although sheath 110a-b could in fact be opaque. Only the distal portion of delivery apparatus 100 is shown in FIG. 1. It will be understood that apparatus 100 continues in the proximal direction (downward and to the left as viewed in FIG. 1), ultimately extending to operator controls, which can be used by an operator (medical practitioner) to (remotely) control the distal portion of the apparatus that is visible in FIG. 1. Whereas the distal portion of apparatus 100 typically enters the patient's body by any of several different routes, the proximal controls tend to remain outside the patient's body where they can be manipulated by the operator.

Principal components of valve 10 are relatively stiff frame 20 and flexible leaflets 30. Because valve 10 is inside delivery apparatus 100, valve 10 is shown in its undeployed, circumferentially relatively small (collapsed) condition. Frame 20 includes three major portions: (1) upstream (blood in-flow side) hollow annular portion 20a, (2) downstream (blood out-flow side) hollow annular portion 20c, and (3) an annular array of axially extending struts 20b that extend between and connect upstream and downstream portions 20a and 20c. When released from apparatus 100, upstream portion 20a annularly expands in the vicinity of the patient's native aortic valve annulus to engage the patient's native tissue in that vicinity. Similarly, when released from apparatus 100, downstream portion 20c annularly expands in the patient's aorta downstream from the valsalva sinus and engages that tissue of the aorta. Further, when valve 10 is released from apparatus 100, struts 20b pass through the patient's valsalva sinus so that these struts continue to link the other portions 20a and 20c of the frame.

The flexible leaflets 30 of the valve 10 are mounted on upstream frame portion 20a so that they are at least primarily inside that frame portion.

Delivery apparatus 100 includes a central-most shaft (not visible in FIG. 1, but coaxial inside shaft 120 and axially movable relative thereto (see FIG. 5 where this central-most shaft is partly visible at 132)). Atraumatic tip 130 is securely mounted on the distal end of this central-most shaft. If desired, delivery apparatus 100 may be insertable into the patient over a guide wire that was previously introduced into the patient. For this purpose, tip 130 may have an axial hole through it and other upstream components may be similarly hollow or provided with an interior lumen. For example, a through hole in tip 130 may connect with a hollow lumen through central-most shaft 132, which lumen may extend proximally until it emerges at the proximal end of the apparatus.

The distal portion 110b of a split outer sheath of apparatus 100 is securely attached to tip 130 and extends proximally therefrom to sheath split or parting line 110c. In particular, parting line 110c is annular and located in the vicinity of the strut portion 20b of valve frame 20. Parting line 110c is at the location where the proximal end of distal sheath portion 110b meets the distal end of proximal sheath portion 110a, and where these two portions of the sheath can be pulled apart when desired. The adjacent ends of these two sheath portions 110a and 110b may initially abut one another at parting line 110c, or they may initially axially overlap one another in the vicinity of parting line 110c. (As used herein, the term axially or the like means parallel to the longitudinal axis of apparatus 100.) From the foregoing it will be seen that when inner-most shaft 132 is moved axially, the entire subassembly of shaft 132, sheath portion 110b, and tip 130 moves together as a unit.

Annularly around the (invisible in FIG. 1) central-most shaft 132 on which tip 130 is mounted is another axially extending longitudinal shaft 120. Shaft 120 is axially movable relative to the above-mentioned central-most shaft. An annular plunger 140 is securely mounted on the distal end of shaft 120. Plunger 140 includes (1) a distal section 140a having a relatively large outer diameter; (2) a proximal section 140c having an outer diameter that alternates between relatively large and relatively small as one proceeds in the annular direction around that section of the plunger; and (3) an intermediate section having a relatively small outer diameter. The above-mentioned relatively large diameters fit with only a relatively small clearance inside sheath 110b. The above-mentioned relatively small diameters are small enough to readily accept the thickness of valve frame 20 between the plunger surface having such relatively small diameter and the inner surface of sheath 110b. Intermediate portion 140b is axially long enough to relatively snugly receive the axial length of the distal portion 20c of valve frame 20. Similarly, struts 20b of valve frame 20 can pass axially through the reduced-diameter regions of the proximal portion 140c of plunger 140.

From the above description it will be appreciated that the distal portion 20c of valve frame 20 is captured radially between the outer surface of the intermediate portion 140b of plunger 140 and the inner surface of the distal sheath portion 110b, and that it is captured axially between the distal portion 140a of plunger 140 and the relatively large diameter portions of the proximal portion 140c of the plunger. There is even rotational securement of valve frame 20 relative to plunger 140 as a result of struts 20b passing through proximal plunger portion 140c between relatively large diameter regions of that proximal portion.

Proximal of valve 10 is another plunger 150 securely mounted to shaft 120 and coaxial (annular) around that shaft. Proximal plunger 150 has a relatively large outer diameter that fits within proximal sheath portion 110a with relatively small clearance.

The structure shown in FIG. 1 can be constructed with any desired degree of lateral flexibility (the opposite of lateral stiffness). (Lateral flexibility refers to the ability of structure 100 to deflect (bend) transverse to its longitudinal axis.) For example, if delivery apparatus 100 is intended for percutaneous delivery of valve 10 into a patient, apparatus 100 may be required to have a relatively high degree of lateral flexibility so that the apparatus can follow the inside of curving vascular passageways inside the patient to reach the desired implant site of valve 10. On the other hand, if apparatus 100 is intended for use in transapical delivery of valve 10 into the patient, it may be desirable for apparatus 100 to be somewhat laterally stiffer than would be best for percutaneous use.

Figure 2:
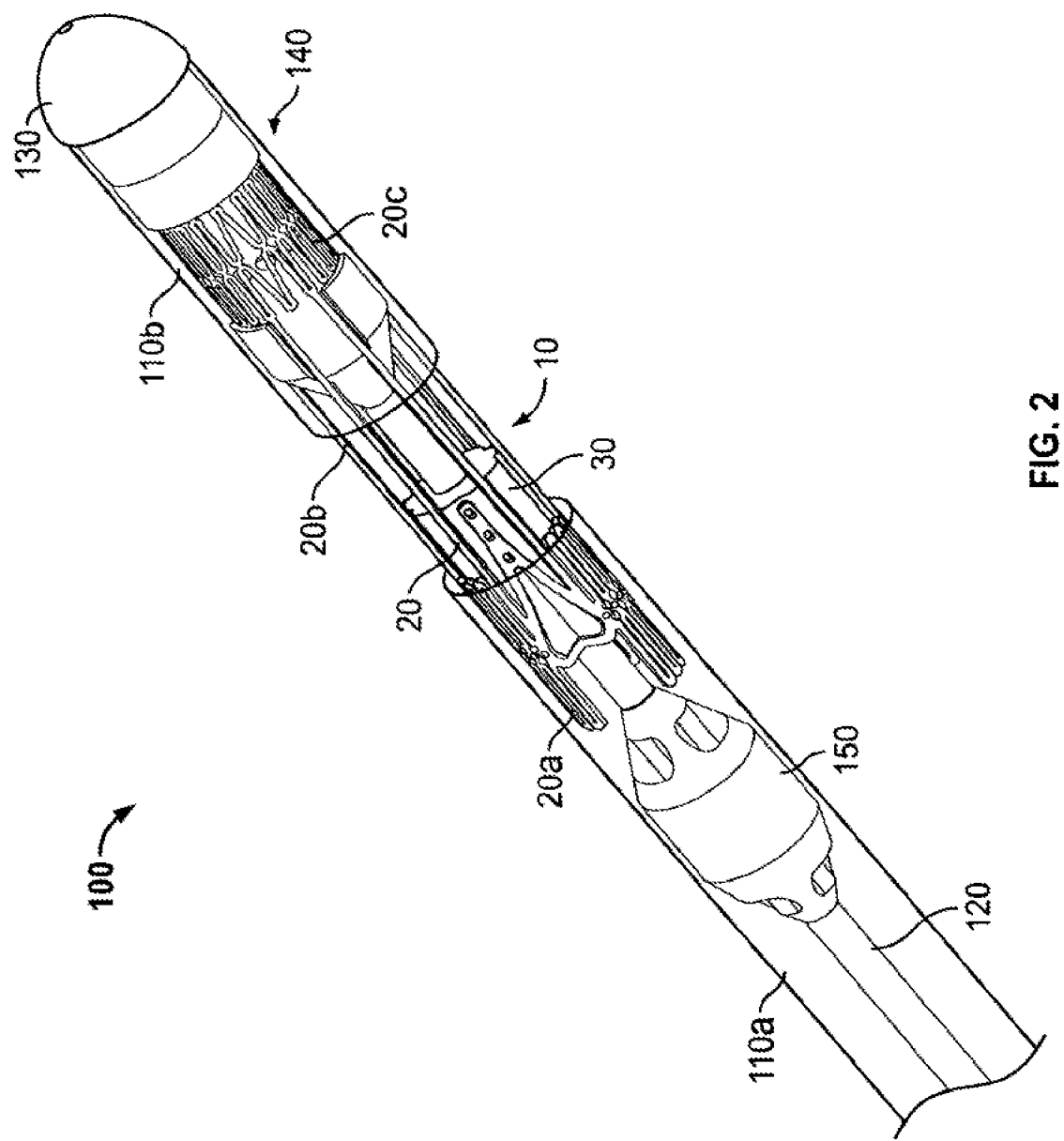
FIG. 2 is similar to FIG. 1 for another operating condition of the FIG. 1 apparatus in accordance with the invention.
Figure 3:
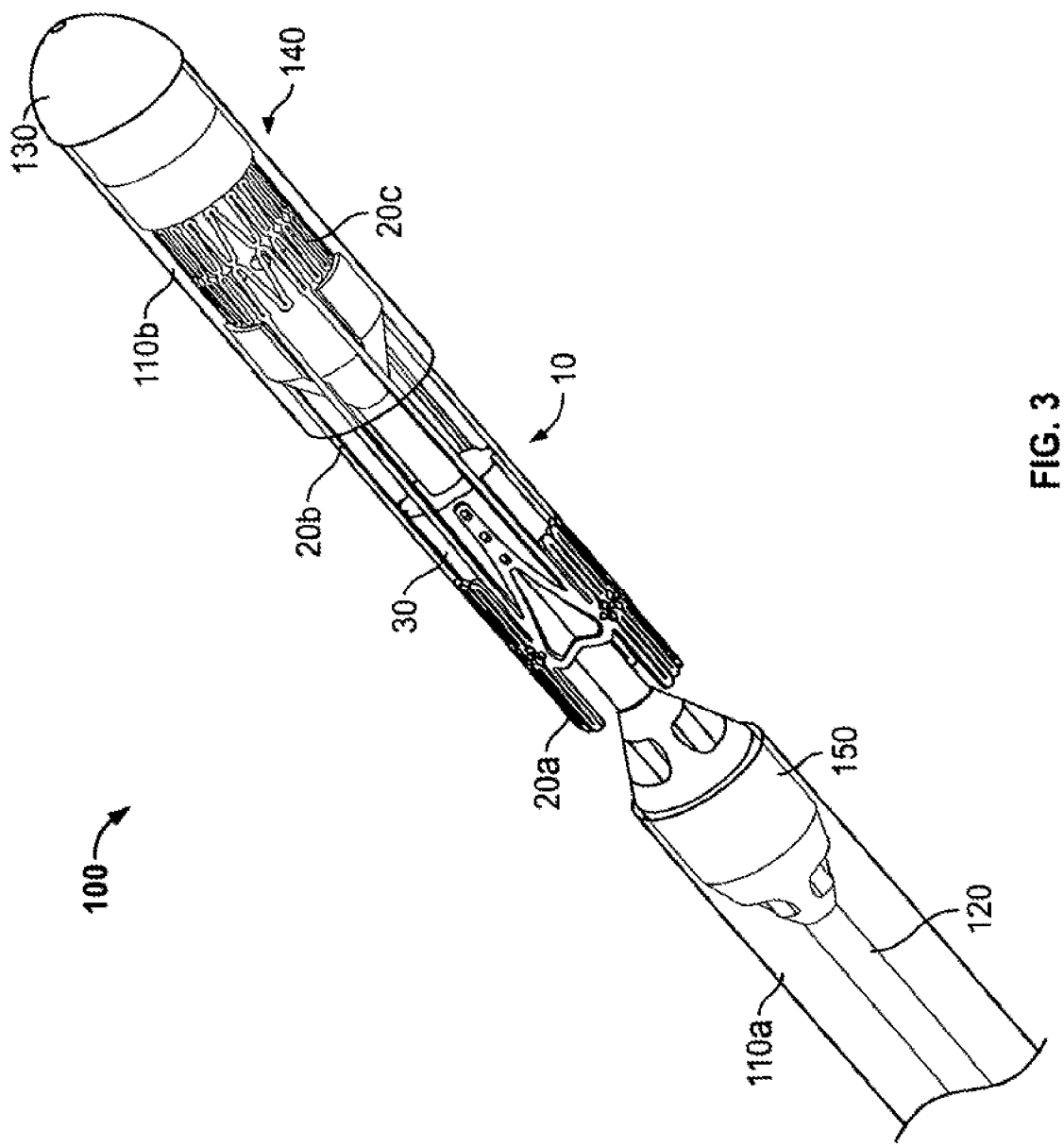
FIG. 3 is again similar to FIG. 1 for still another operating condition of the FIG. 1 apparatus in accordance with the invention.
Figure 4:
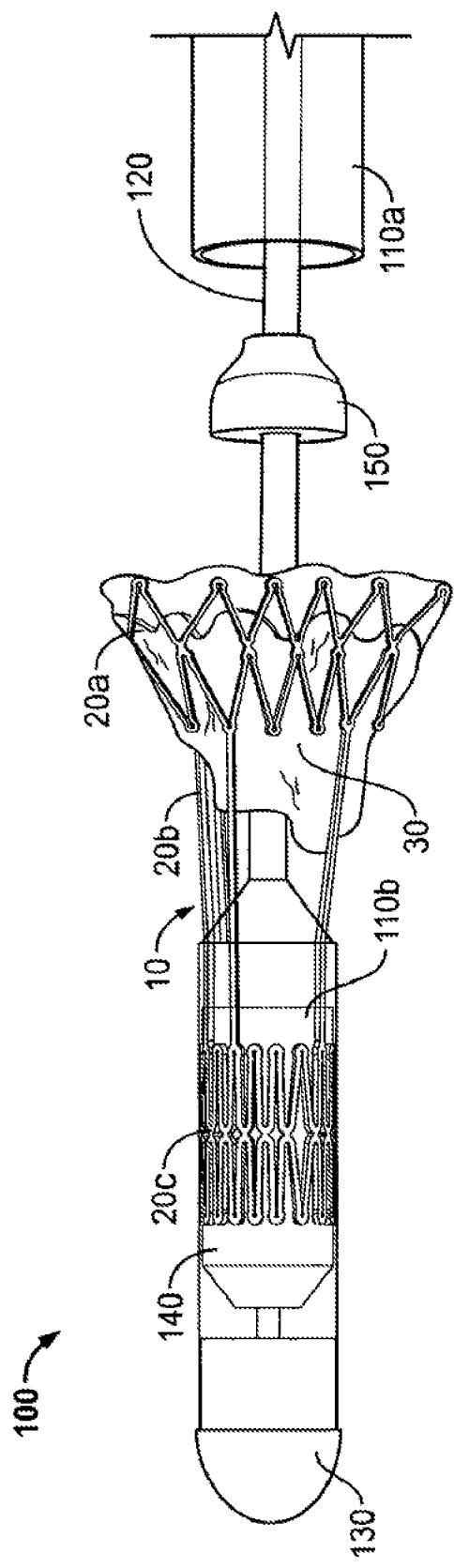
FIG. 4 is a simplified elevational view of portions of another illustrative embodiment of apparatus in accordance with the invention.

FIG. 2 shows one example of how the FIG. 1 apparatus may be operated to begin to deploy valve 10 in a patient. In this example, when valve 10 is at the intended implant site in the patient, proximal sheath 110a is pulled back proximally relative to everything else in FIG. 2. This begins to expose the proximal portions of valve 10. However, the distal portions of valve 10 remain securely held by the distal portions of delivery apparatus 100. This manipulation of delivery apparatus 100 can continue until (as shown in FIGS. 3 and 4) the entire proximal portion of valve 10 has been exposed. FIG. 3 shows this result in simplified form, which omits depiction of the consequent radial enlargement of the proximal portion of valve 10. However, FIG. 4 does show the proximal portion 20a of valve 10 enlarging radially outward as a result of its release from constraint by proximal sheath 110a. (All of the enlargement of the valve depicted and/or described herein may be due to resilient and/or shape-memory enlargement of valve frame 20. Shape-memory enlargement may be partially controlled by controlling the ambient temperature that valve frame 20 is exposed to.)

Figure 5:
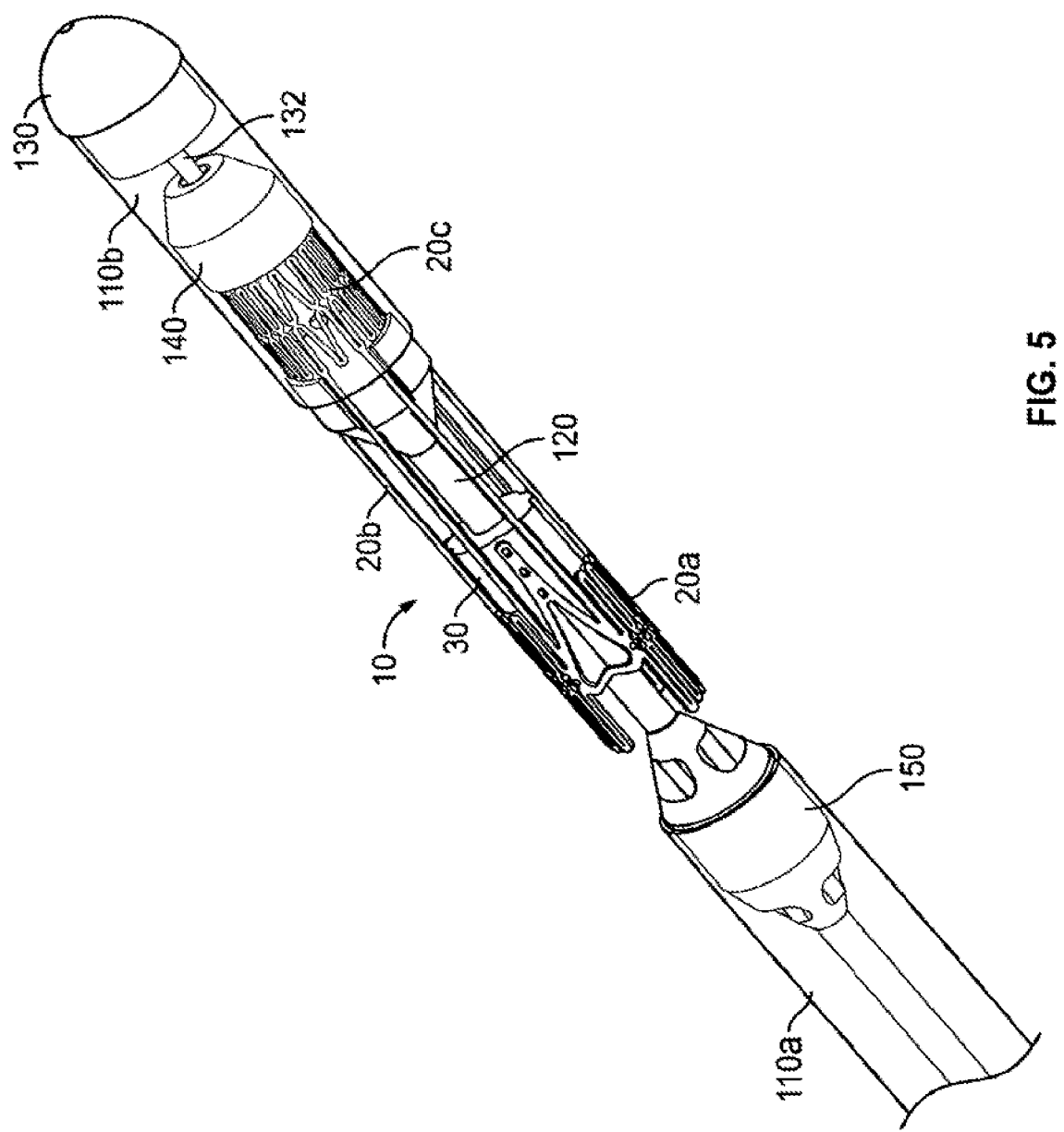
FIG. 5 is again similar to FIG. 1 for yet another operating condition of the FIG. 1 apparatus in accordance with the invention.

FIG. 5 shows further deployment of valve 10 (after the condition shown in FIGS. 3 and 4 has been reached). (Again, FIG. 5 is simplified by not showing the radial enlargement of the proximal portion of valve 10.) In FIG. 5 tip 130 is pushed distally relative to other structure in the FIG. by pushing the shaft 132 (on which tip 130 is mounted) distally relative to shaft 120. (Shaft 132 was mentioned earlier, but it was not visible in the FIGS. prior to FIG. 5.) As tip 130 moves distally, it carries distal sheath portion 110b with it, thereby beginning to expose the distal portion of valve 10, which distal valve portion (at least initially) continues to be held securely by plunger 140 inside distal sheath portion 110b.

Figure 6:
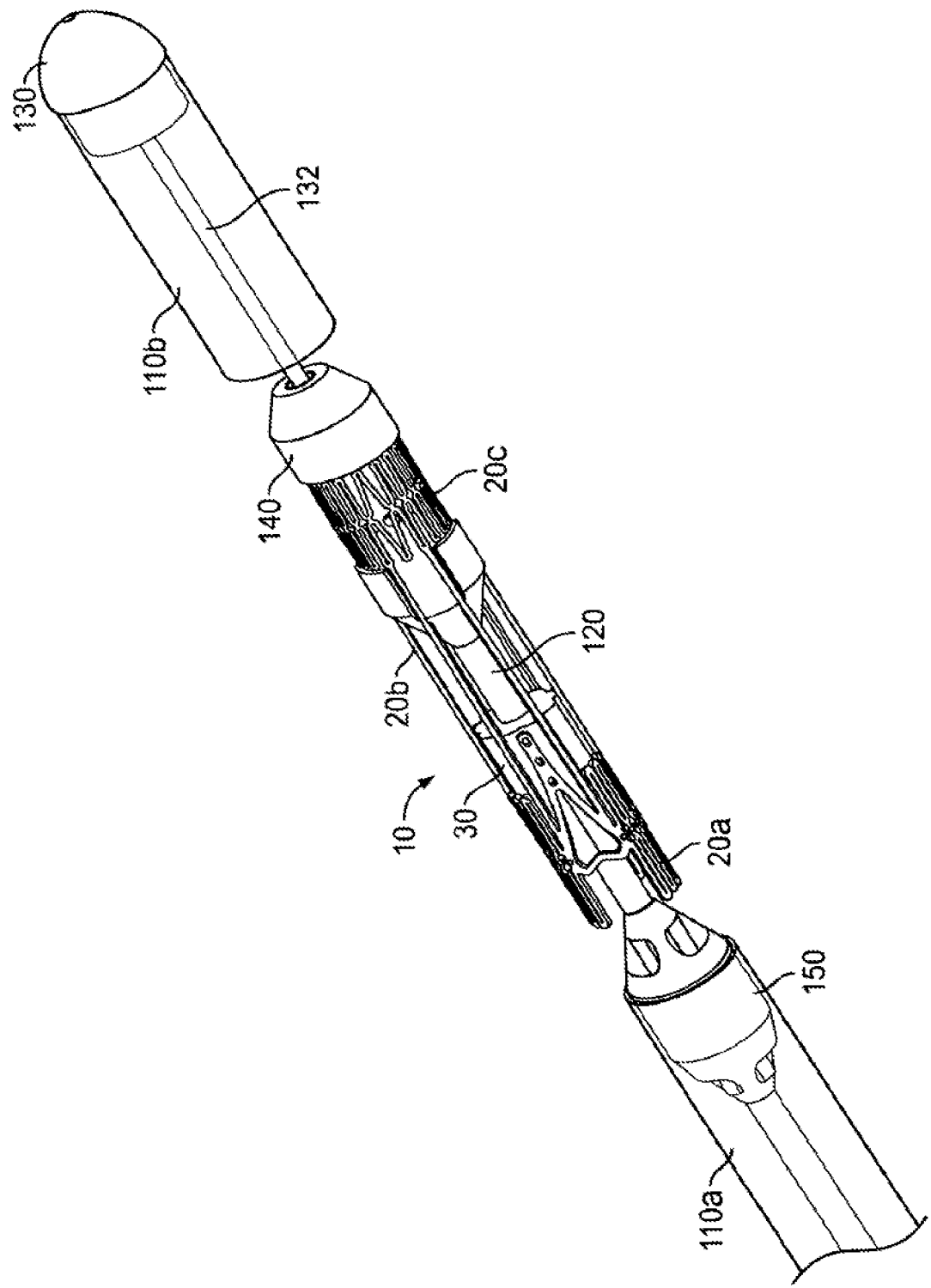
FIG. 6 is again similar to FIG. 1 for still another operating condition of the FIG. 1 apparatus in accordance with the invention.

FIG. 6 shows the condition of the FIG. 5 apparatus after distal sheath 110b has moved completely beyond the distal end of valve 10 and the valve is therefore completely exposed and deployed in the patient (except that FIG. 6 again omits the fact that at this stage valve 10 will have annularly enlarged along its entire length to engage surrounding native body tissue of the patient, thereby anchoring the valve at the desired implant site in the patient). After valve 10 has thus annularly enlarged and deployed in the patient, the valve delivery apparatus 100 can be withdrawn from the patient. To facilitate such withdrawal, proximal sheath portion 110a can be pushed distally relative to other components through the leaflet structure 30 of the valve. Distal tip 130 and distal sheath portion 110b can then be pulled proximally relative to other components until the proximal end of sheath 110b meets the distal end of sheath 110a (or, as in other embodiments, until distal sheath portion 110b is inside proximal sheath portion 110a), thereby again giving delivery apparatus 100 a smooth outer surface. This facilitates withdrawal of apparatus 100 in the proximal direction through deployed valve 10 without compromising leaflets 30.

Figure 7:
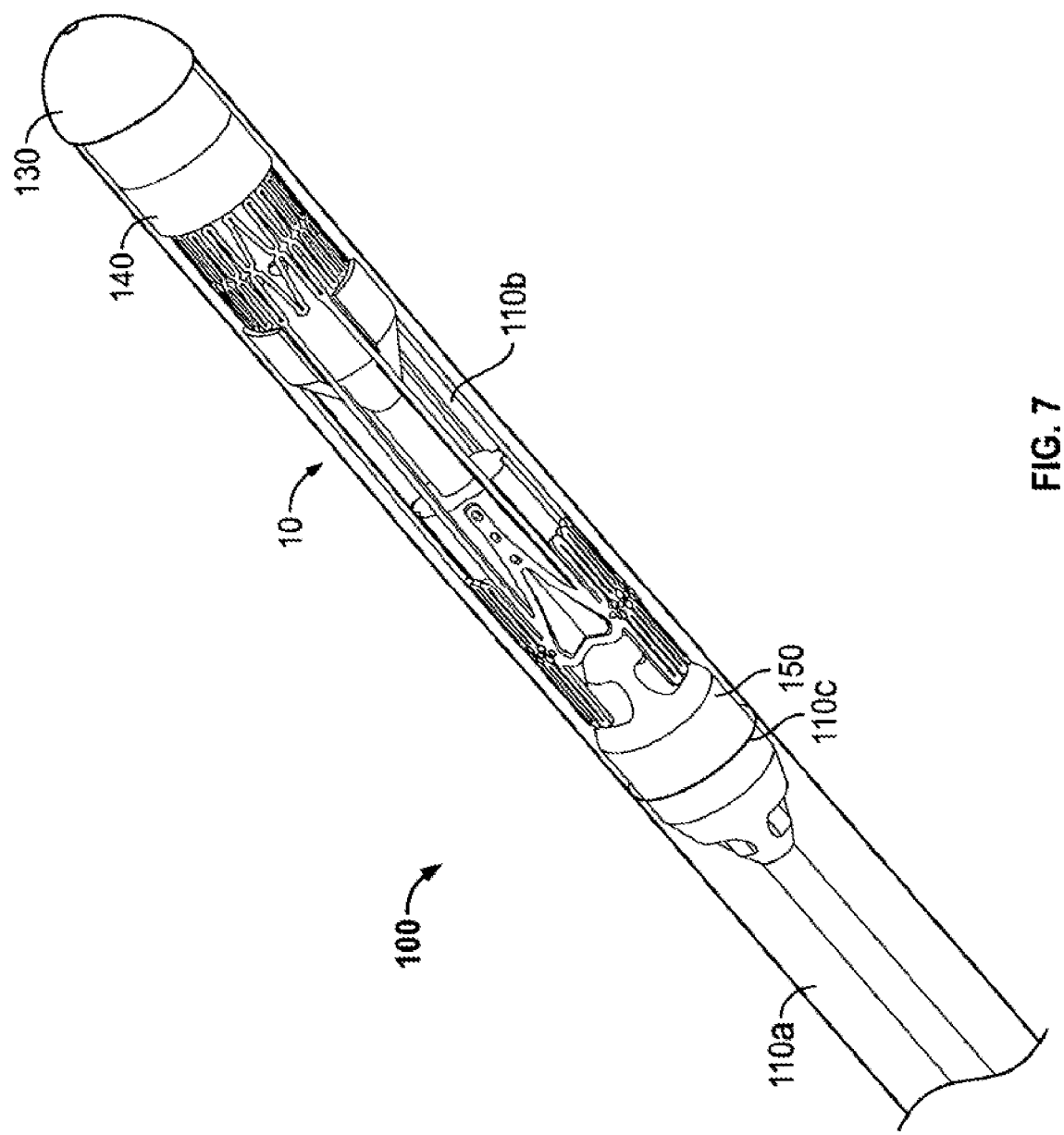
FIG. 7 is a view similar to FIG. 1 for portions of another illustrative embodiment of apparatus in accordance with the invention.

FIG. 7 shows two possible variations from earlier-described embodiments. (The general reference number 100 continues to be used for the delivery apparatus, even though there are some variations from earlier embodiments.) One of these possible variations is use of proximal end retainer 150 so that the proximal end of valve 10 can rest on it, thereby controlling the collapsed inside diameter of the valve. The other possible variation is relocating the split 110c between the proximal sheath portion 110a and the distal sheath portion 110b so that split 110c is proximal of valve 10. The valve is now deployed solely by moving distal sheath portion 110b distally to a final position like that shown in FIG. 8. In other words, moving distal sheath portion 110b (which initially completely covers valve 10) in the distal direction completely uncovers the valve for deployment in the patient. (FIG. 8 again omits depiction of the annular enlargement of valve 10 that follows from moving sheath 110b away to expose the valve.)

Figure 9:
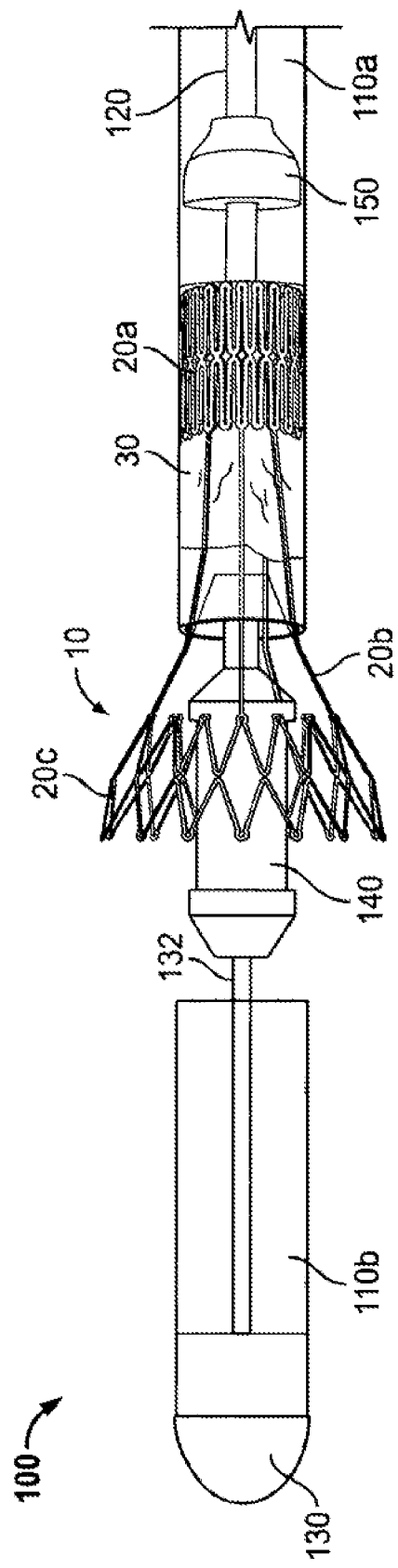
FIG. 9 is a simplified elevational view of portions of still another illustrative embodiment of apparatus in accordance with the invention.

Returning to embodiments like those shown in FIGS. 1-6, FIG. 9 shows a possible alternate use. This alternate use is deployment of the distal portion 20c first. This is accomplished by shifting elements 130, 132, and 110b distally relative to other components before shifting sheath portion 110a proximally. This is the condition of the apparatus that is shown in FIG. 9; and as that FIG. shows, it results in release and annular enlargement of the distal portion 20c of valve 10, while the proximal portion 20a is still confined within proximal sheath portion 110a. The condition shown in FIG. 9 will be followed by shifting sheath portion 110a proximally, which exposes and deploys (i.e., allows annular enlargement of) the proximal portion 20a of valve 10.

Figure 10:
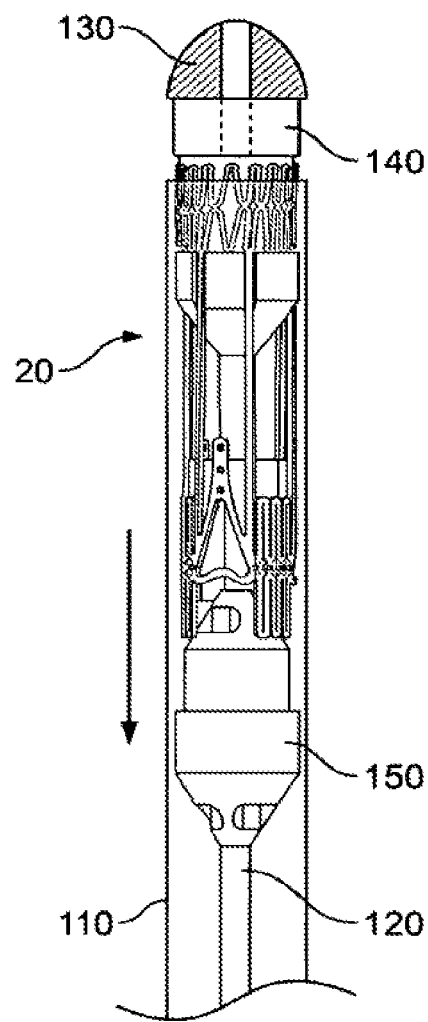
FIG. 10 is a simplified elevational view of portions of yet another illustrative embodiment of apparatus in accordance with the invention.

FIG. 10 shows yet another alternative in which sheath 110 is not divided into two axially different parts. Instead, in FIG. 10 one sheath 110 extends all the way to distal tip 130. However, sheath 110 can be pulled proximally back from distal tip 130 when valve 20 is at the desired location in the patient. FIG. 10 shows such proximal retraction of sheath 110 beginning. This exposes (and deploys) valve 20 distal end first.

Figure 11:
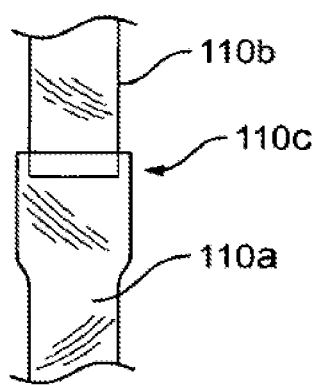
FIG. 11 is a simplified elevational view of portions of still another illustrative embodiment of apparatus in accordance with the invention.
Figure 12:
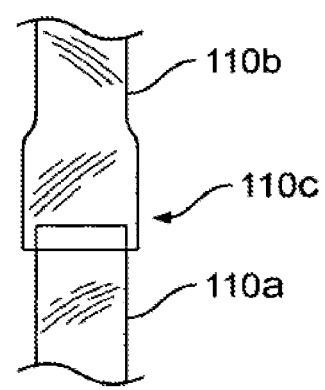
FIG. 12 is a simplified elevational view of portions of yet another illustrative embodiment of apparatus in accordance with the invention.

FIGS. 11 and 12 show some possible ways that the parts 110a and 110b of an axially split sheath 110 may come together. In FIG. 11 a distal portion of part 110a is slightly enlarged so that it can fit around the outside of the proximal portion of part 110b. In the alternative shown in FIG. 12 this arrangement is reversed. In particular, in FIG. 12 the proximal portion of part 110b is slightly enlarged so that it can fit around the outside of the distal portion of part 110a. Other variations are possible, such as having the ends of parts 110a and 110b the same size so that they simply abut one another with no overlapping (as they do in FIGS. 11 and 12).

Figure 13:
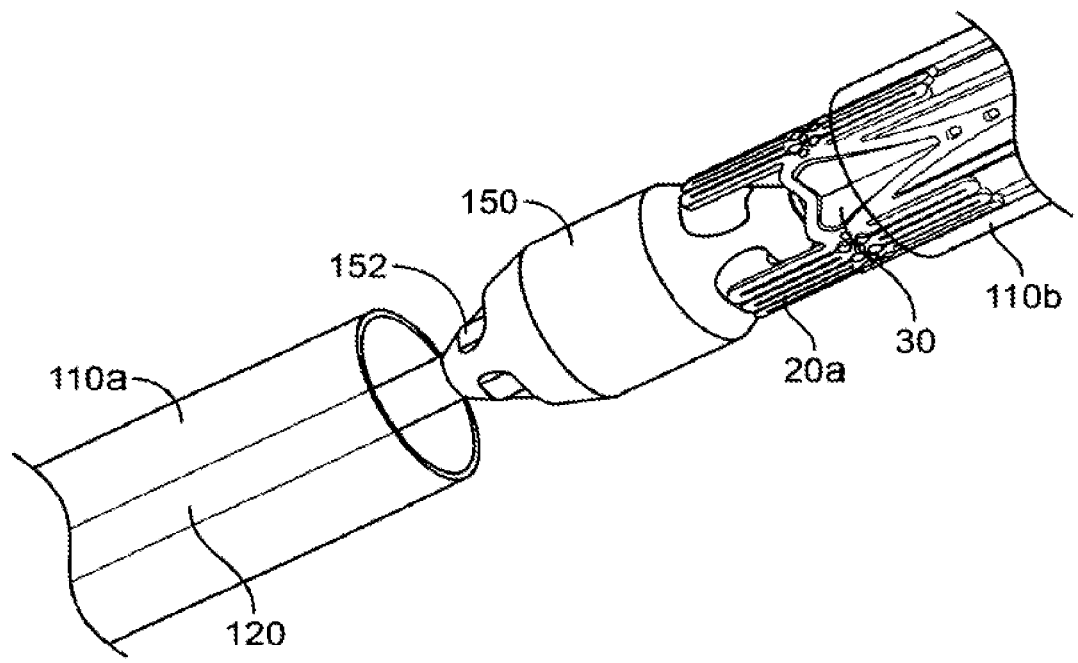
FIG. 13 is a simplified isometric or perspective view of portions of still another illustrative embodiment of apparatus in accordance with the invention.

FIG. 13 shows possible construction of proximal end retainer 150 with holes 152 extending axially through. These holes can allow fluid to pass from proximal portions of the delivery apparatus, through retainer 150, to reach valve 20. For example, such fluid can have a temperature that is controlled to cool or warm the valve to help it deploy into the patient in a controlled manner (e.g., using shape-memory properties of the frame 20 of valve 10 when that frame is made of a material like nitinol).

Figure 14:
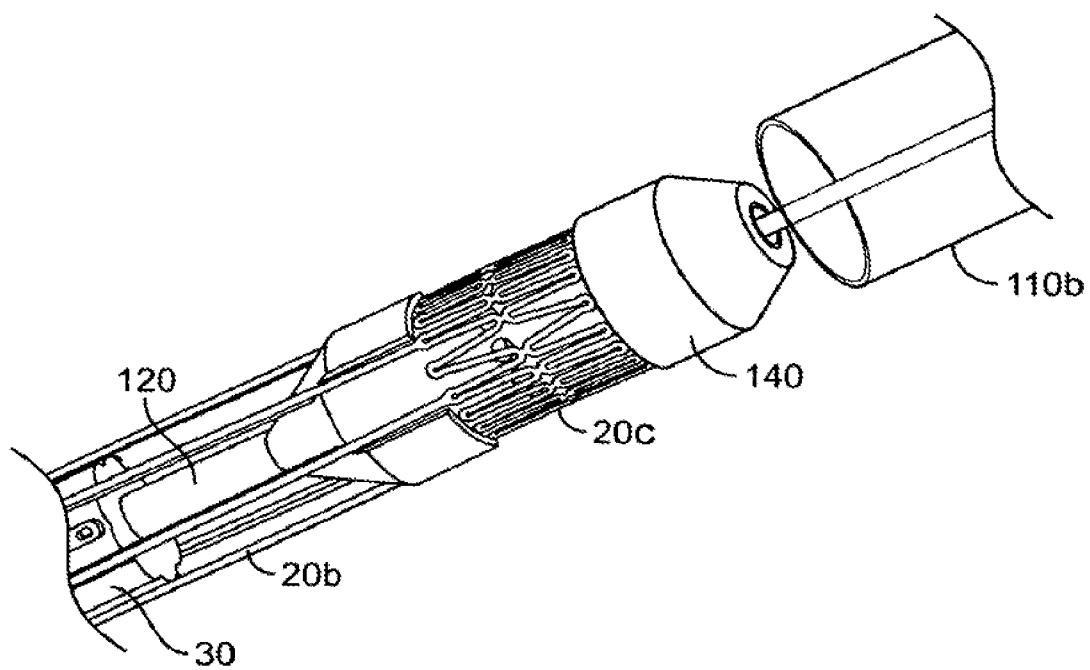
FIG. 14 is a simplified isometric or perspective view of portions of yet another illustrative embodiment of apparatus in accordance with the invention.

FIG. 14 is an enlargement of distal end retainer 140 in which its possible construction can perhaps be seen more clearly.

Figure 15:
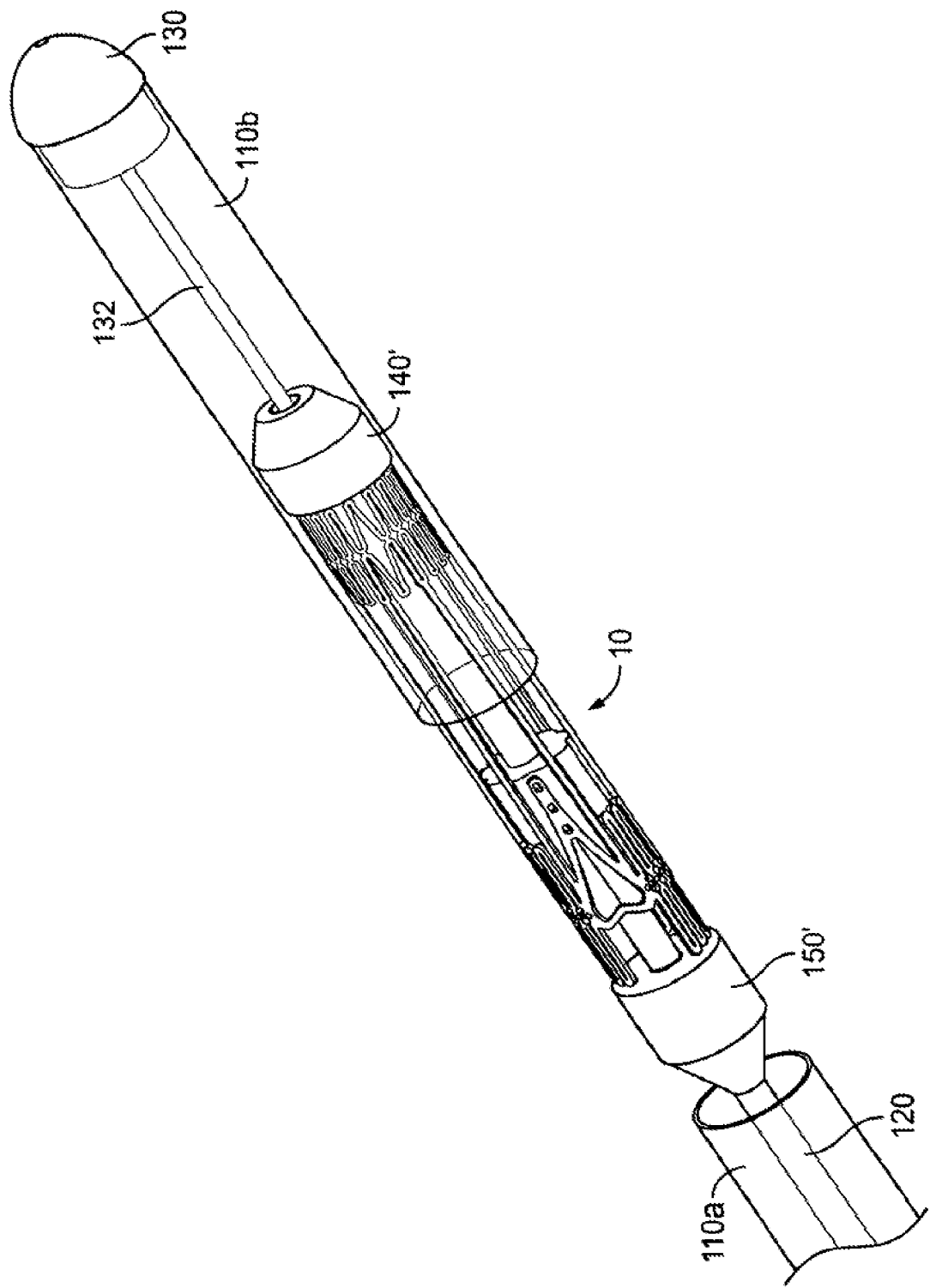
FIG. 15 is a simplified isometric or perspective view of portions of still another illustrative embodiment of apparatus in accordance with the invention.

FIG. 15 shows an alternate design in which a "bumper" 140' or 150' is mounted on shaft 120 adjacent each axial end of the frame 20 of valve 10. Each bumper has a face that is perpendicular to the longitudinal axis of the apparatus and that faces toward the axial end of valve frame 20 that is adjacent to that bumper. These bumper faces keep valve 10 trapped at the desired axial location in the delivery apparatus until the valve is exposed and therefore able to annularly enlarge as a result of the axial shifting of sheath portions 110a and 110b. The faces of bumpers 140' and 150' that face away from valve 10 are preferably conical as shown. This helps sheath portions 110a and 110b to again come together after valve deployment, when a smooth exterior of apparatus 100 is again desired to facilitate withdrawal of the delivery apparatus from the patient.

Figure 16:
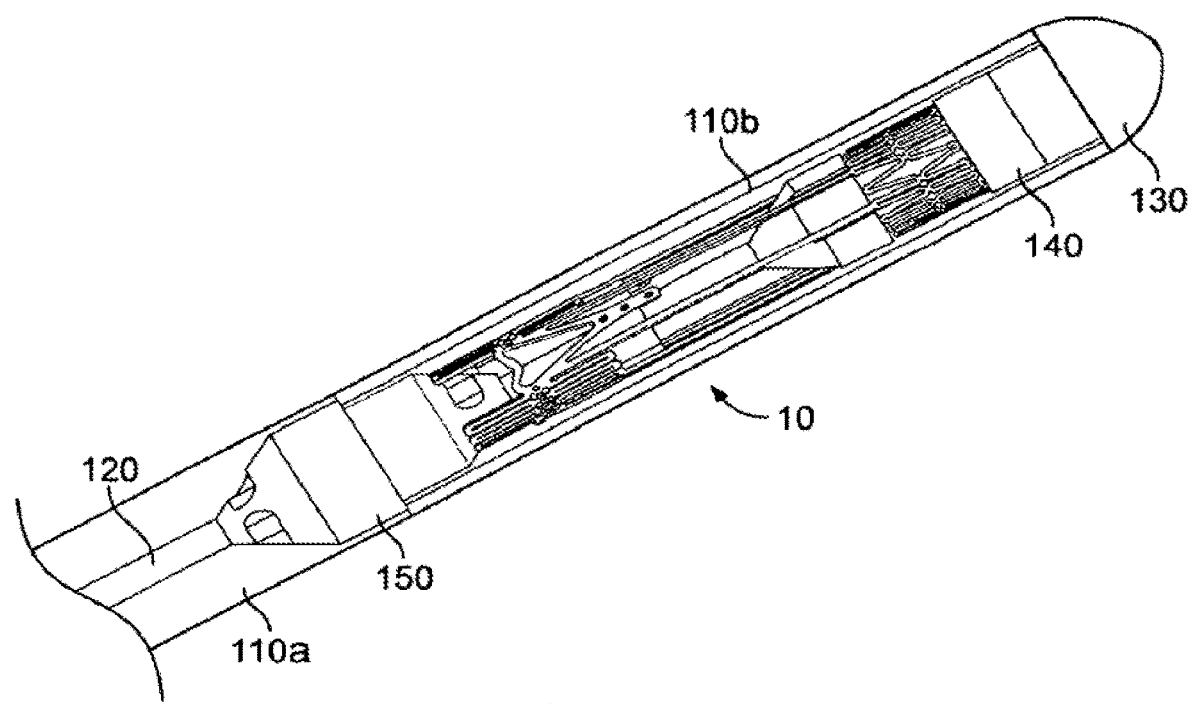
FIG. 16 is a simplified elevational view of portions of yet another illustrative embodiment of apparatus in accordance with the invention.
Figure 17:
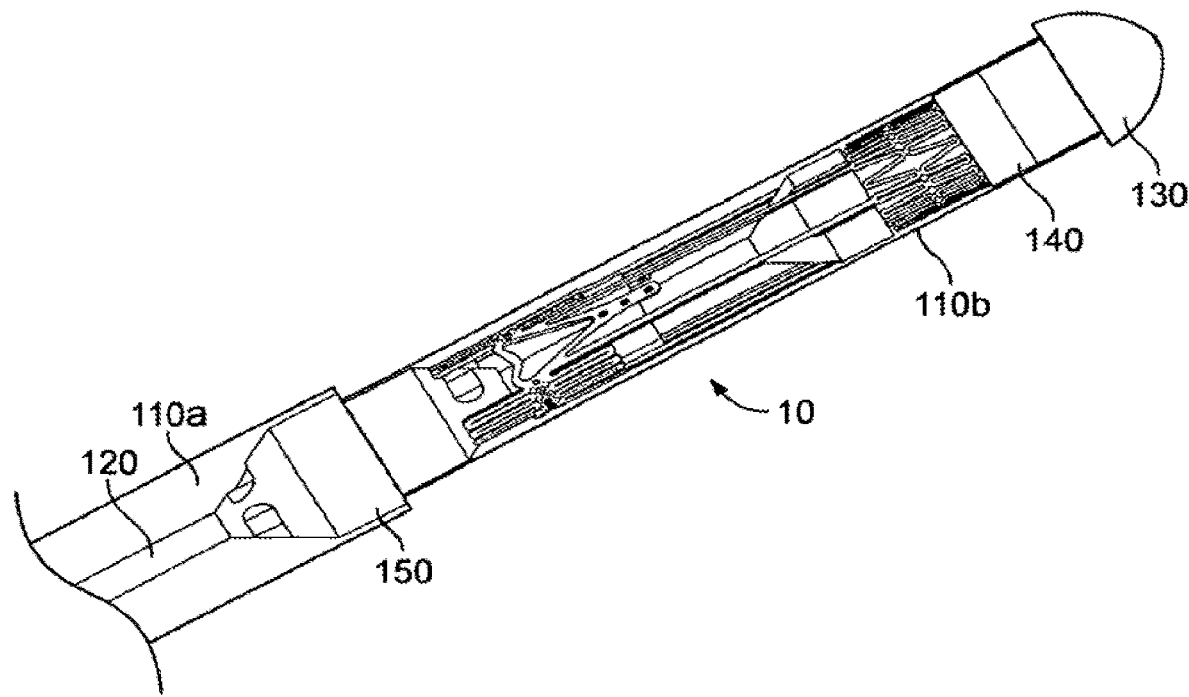
FIG. 17 is similar to FIG. 16 for another operating condition of the FIG. 16 apparatus in accordance with the invention.
Figure 18:
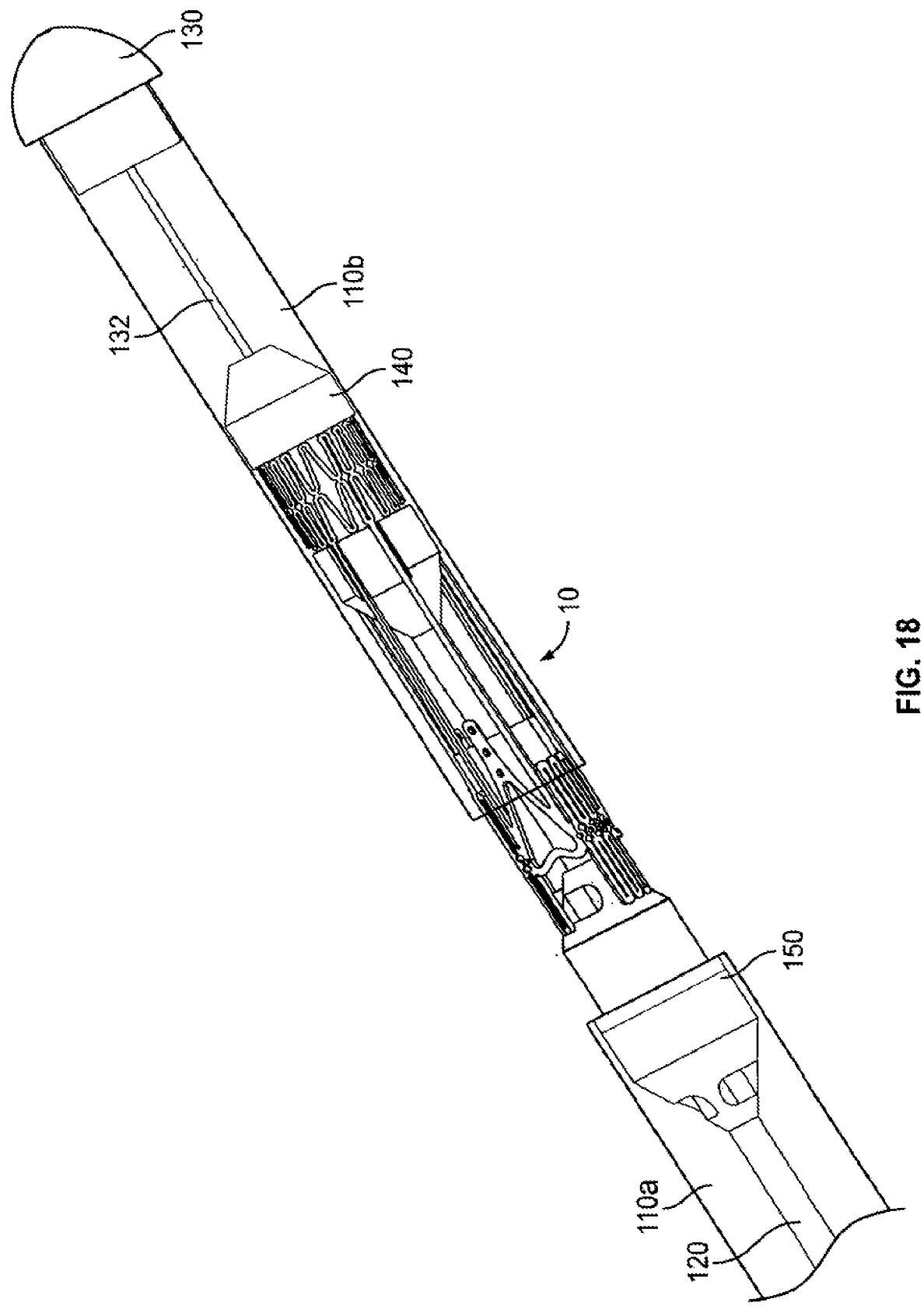
FIG. 18 is again similar to FIG. 16 for yet another operating condition of the FIG. 16 apparatus.

FIGS. 16-18 illustrate another possible construction of delivery apparatus 100. In this construction proximal sheath part 110a initially extends distally all the way to distal tip 130. Inside the distal portion of sheath 110a, distal sheath portion 110b extends proximally from distal tip 130 to initially completely cover valve 10 (i.e., it ends with some overlap of the distal part of plunger 150). Valve 10 is deployed by first pulling sheath 110a back proximally so that its distal end is adjacent plunger 150 as shown in FIG. 17. No part of the valve is yet deployed, however, because the valve is still entirely inside sheath 110b. Then distal tip 130 and sheath 110b can be pushed distally to begin to expose valve 10 as shown in FIG. 18. This exposure of the valve starts at the proximal end (as shown in FIG. 18), and then continues until the valve is completely exposed and deployed. (Once again, FIG. 18 omits depiction of the annular enlargement of valve 10 that occurs when the valve is exposed.)

A possible variation of what is shown in FIGS. 16-18 is to make distal sheath 110b shorter so that the proximal end of the valve begins to deploy when the proximal sheath 110a is retracted beyond the proximal end of distal sheath 110b.

Figure 19:
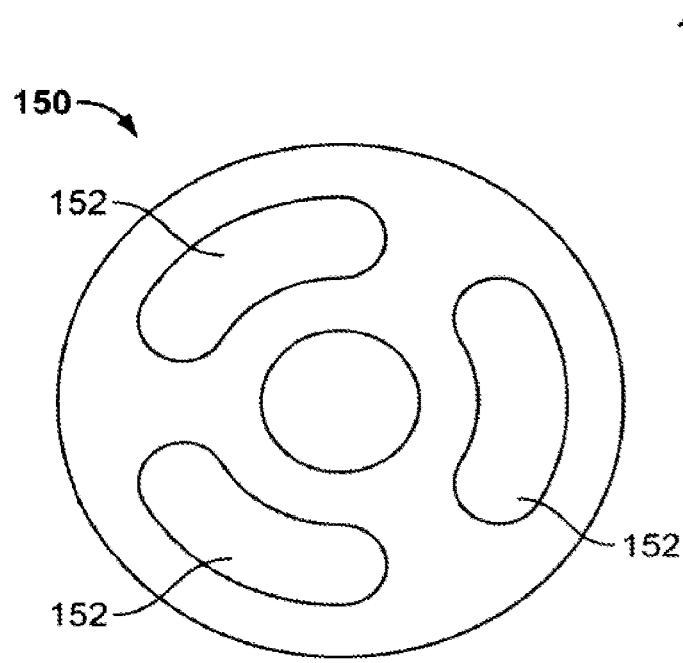
FIGS. 19 and 20 are simplified elevational views, taken at right angles to one another, of an illustrative embodiment of a component of apparatus in accordance with the invention.
Figure 20:
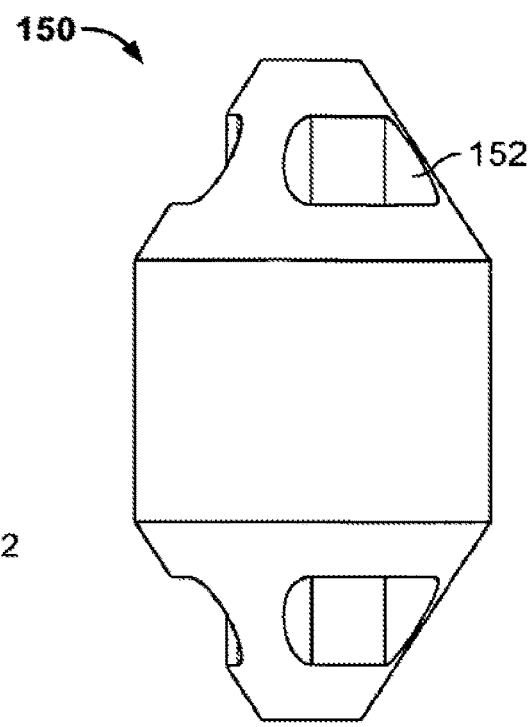
Figure 21:
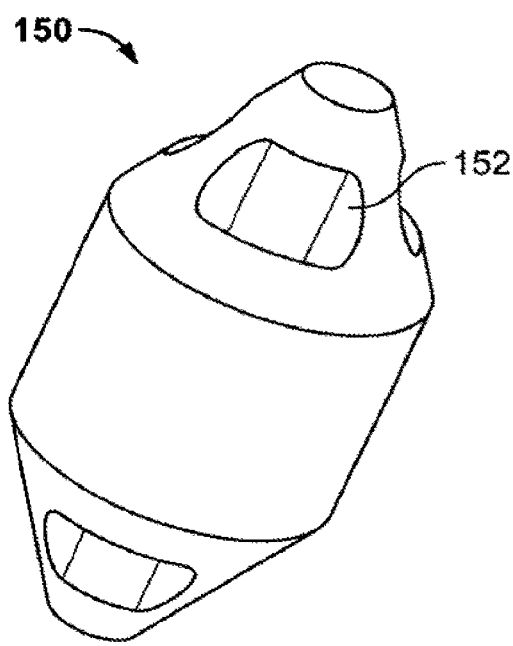
FIG. 21 is a simplified isometric or perspective view of the component shown in FIGS. 19 and 20.
Figure 22:
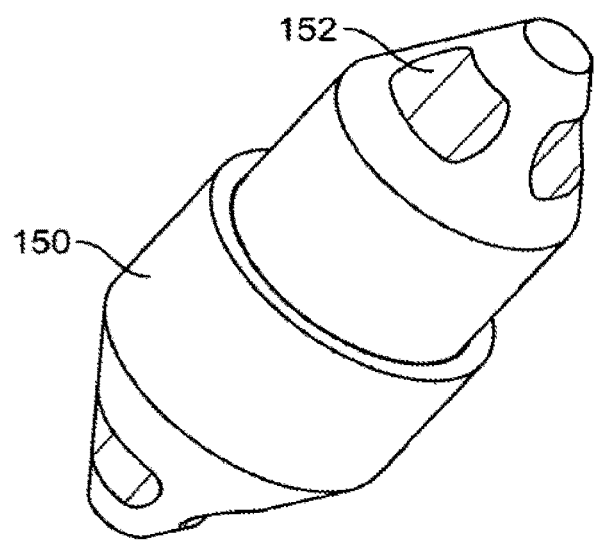
FIG. 22 is a simplified isometric or perspective view of an alternative embodiment of the component shown in FIGS. 19-21 in accordance with the invention.
Figure 23:
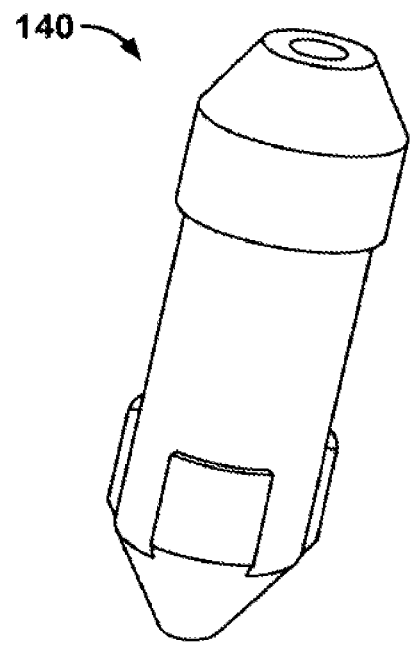
FIG. 23 is a simplified isometric or perspective view of an illustrative embodiment of another component of apparatus in accordance with the invention.
Figure 24:
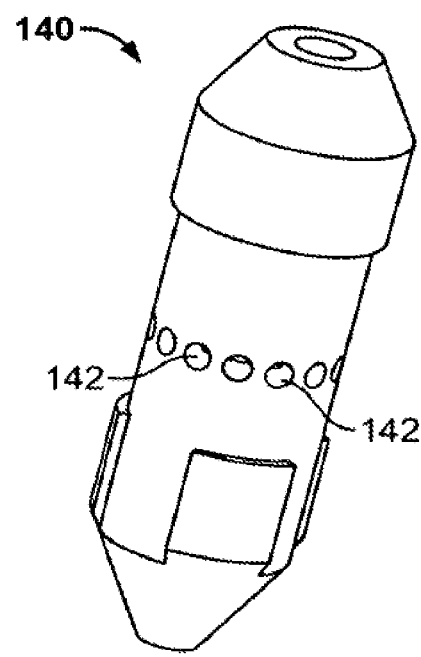
FIG. 24 is a simplified isometric or perspective view of an alternative embodiment of the FIG. 23 component in accordance with the invention.

FIGS. 19-21 show several views of an illustrative embodiment of proximal retainer 150. FIG. 22 shows an alternative embodiment of retainer (like the embodiment used in FIG. 16-18). FIG. 23 shows an illustrative embodiment of distal retainer 140. FIG. 24 shows an alternative embodiment of distal retainer 140 including an annular array of radially extending holes 142 that are usable in an embodiment of delivery apparatus 100 that permits valve 10 to be recollapsed after it has been deployed or partly deployed (e.g., to allow repositioning or removal of the valve).

Delivery apparatus features like this are described in more detail later in this specification.

Figure 25:
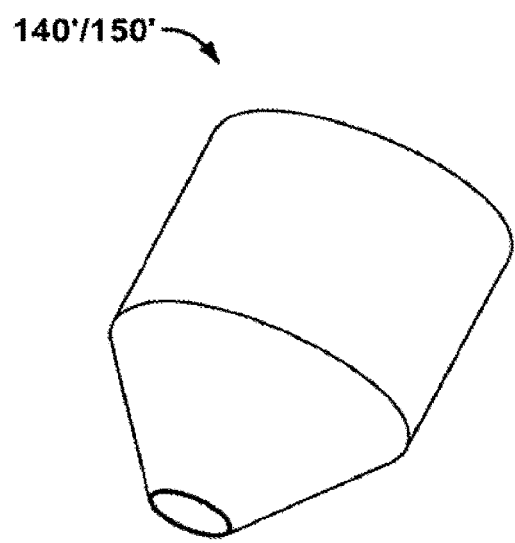
FIGS. 25 and 26 are simplified isometric or perspective views of illustrative embodiments of other components of apparatus in accordance with the invention.

FIG. 25 is another view of an illustrative embodiment of a typical one of above-described bumpers 140'/150'.

Figure 26:
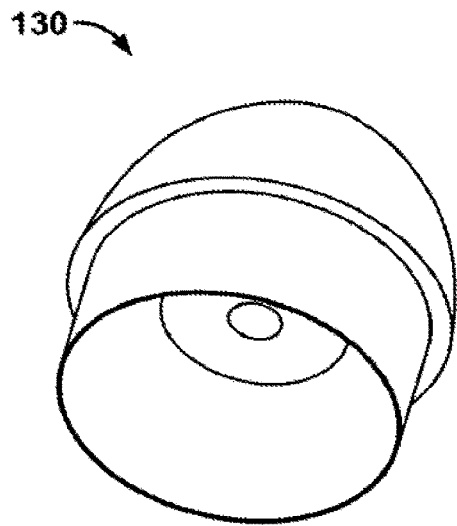

FIG. 26 is another view of an illustrative embodiment of distal tip member 130.

Figure 8:
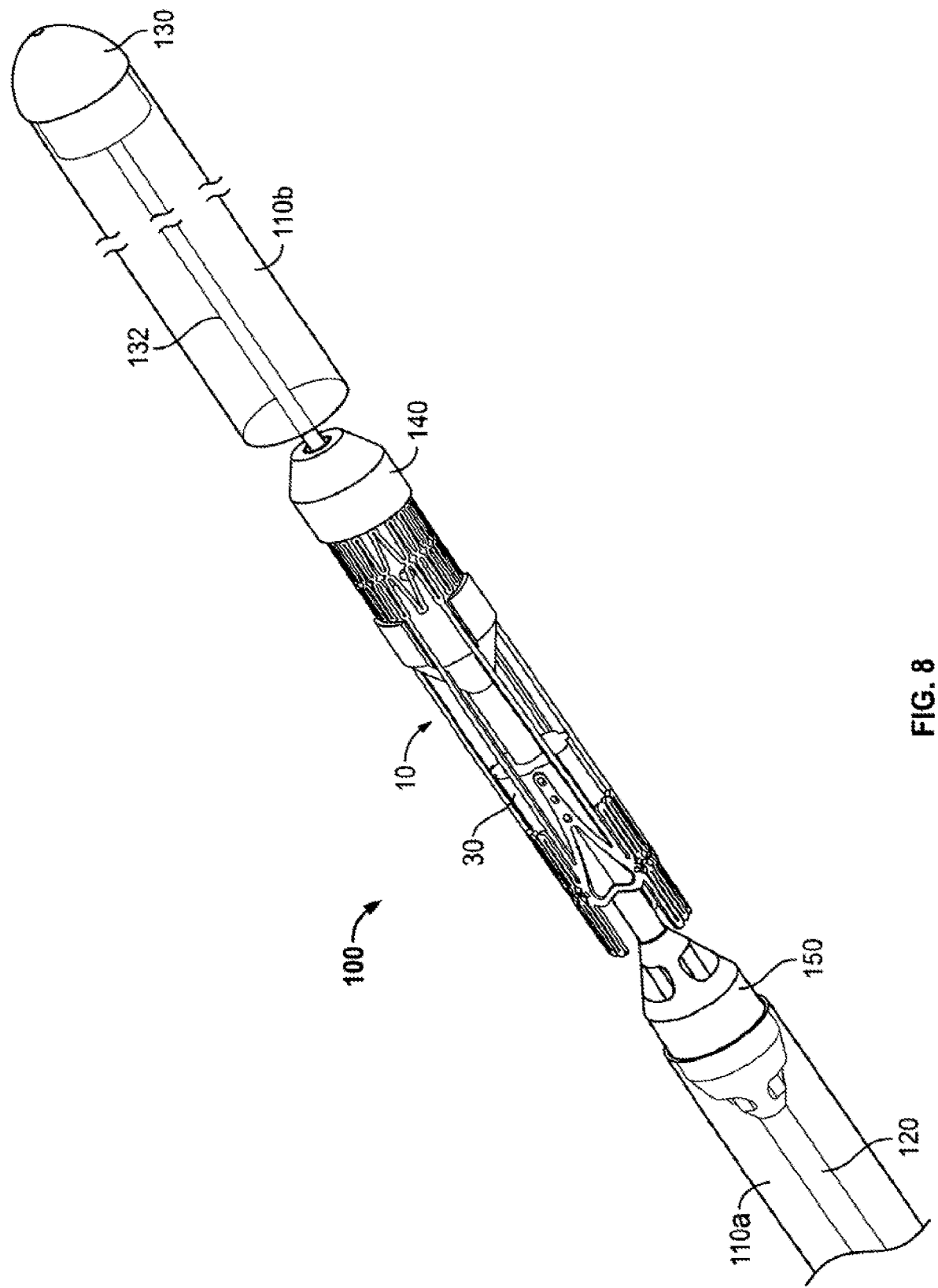
FIG. 8 is similar to FIG. 7 for another operating condition of the FIG. 7 apparatus in accordance with the invention.
Figure 27:
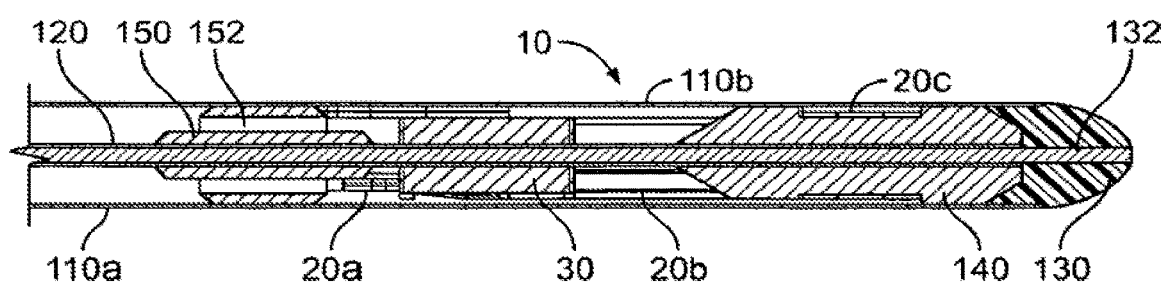
FIG. 27 is a simplified elevational view, partly in section, of an illustrative embodiment of portions of apparatus in accordance with the invention.

FIG. 27 is a longitudinal sectional view of an embodiment like the one shown in FIGS. 7 and 8.

Figure 28:
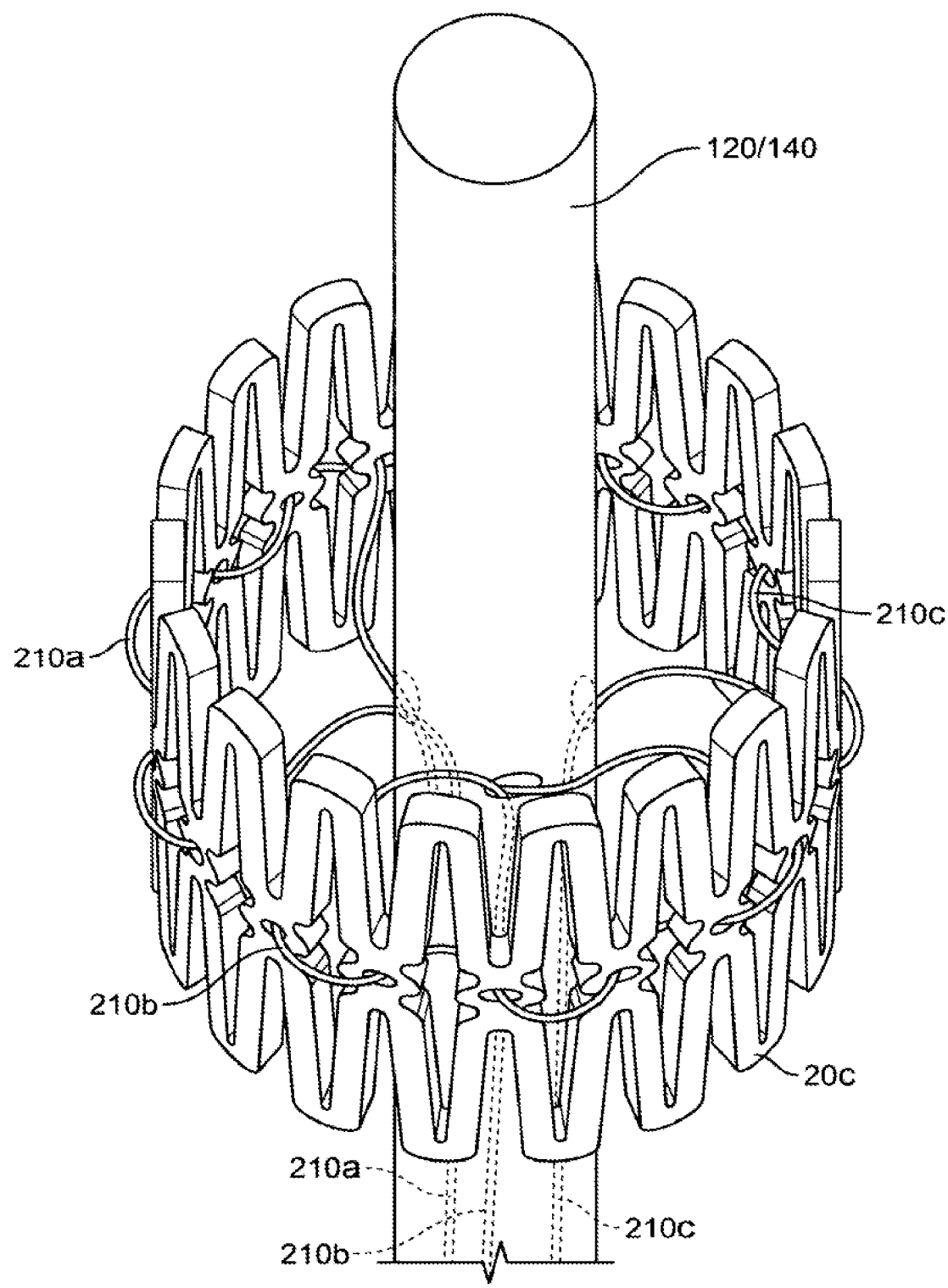
FIG. 28 is a simplified perspective or isometric view of an illustrative embodiment of portions of apparatus in accordance with the invention.

FIG. 28 shows an illustrative embodiment of structures in accordance with certain possible aspects of the invention for facilitating recollapsing of a valve 10 for such purposes as allowing the valve to be repositioned in the patient or removed from the patient after it has been at least partly deployed in the patient but before final release of the valve from the delivery apparatus. FIG. 28 shows only the distal part 20c of the valve 10 (the other parts of the valve being omitted for clarity). As shown in FIG. 28 (and also FIG. 29), three strands 210a-c of flexible recollapsing material are threaded through the distal part 20c of the frame (stent) of valve 10. For example, FIG. 29 more clearly shows that each of these strands 210 is threaded through a respective one of three different arcuate segments of the annulus of distal part 20c. Eyelets (visible in FIG. 28) may be provided in part 20c for threading strands 210 through. Each strand may follow a woven or serpentine trajectory, alternately into and out of the interior of part 20c, as one proceeds in the annular direction around part 20c. The ends of each strand 210 that extend from part 20c enter the lumen of delivery system structure 120 via radial apertures 142 through the side wall of distal retainer 140 as in FIG. 24, which distal retainer is attached to structure 120. Once inside the above-mentioned lumen, these strand ends extend along the lumen in the proximal direction to where they become accessible to control by the operator of the delivery apparatus from outside the patient's body. It is preferred that the apertures (like 142 in FIG. 24) be in approximately the same plane (substantially perpendicular to the longitudinal axis of the delivery apparatus) as the threading of strands 210 through part 20c. In this way, when the ends of strands 210 are pulled proximally (parallel to the longitudinal axis of the delivery apparatus), the above-mentioned apertures (like 142) convert the tension in the strands to radial inward forces on part 20c. Because these forces are radial, they have the greatest efficiency in pulling in on part 20c and thereby re-collapsing that part (e.g., against the outer surface of component 140). Such radial inward force is also preferred because it tends to avoid axial shifting of valve 10 during any re-collapsing operation.

Figure 29:
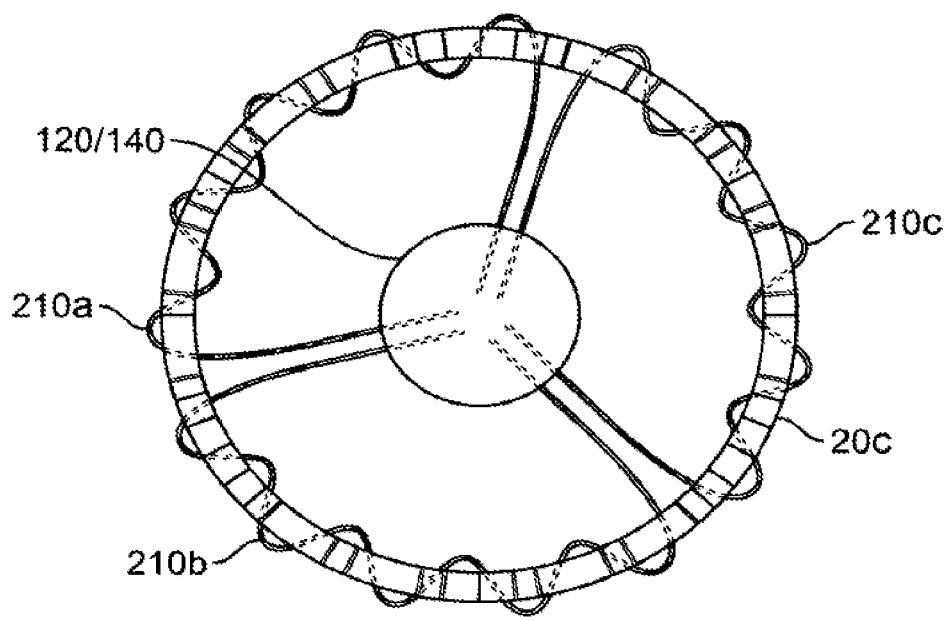
FIG. 29 is a simplified elevational view of an illustrative embodiment of portions of apparatus in accordance with the invention.
Figure 30:
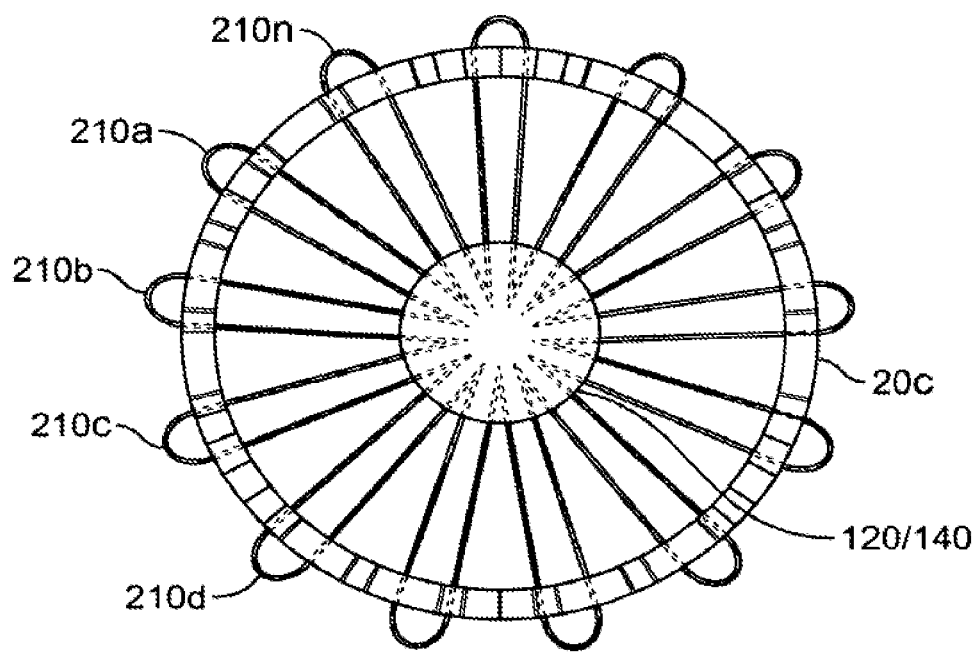
FIG. 30 is a view similar to FIG. 29 for another illustrative embodiment in accordance with the invention.
Figure 31:
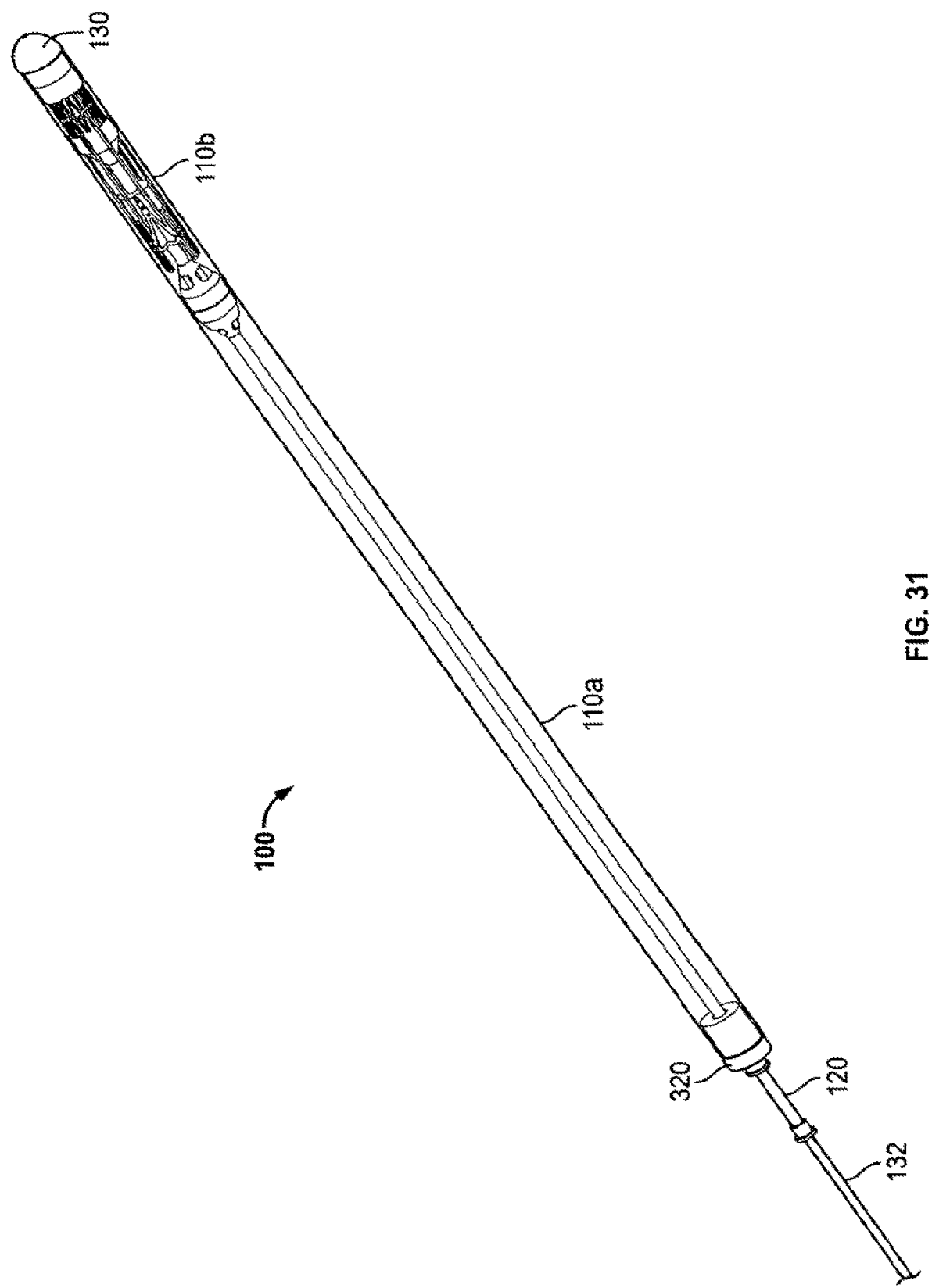
FIG. 31 is a simplified isometric or perspective view of portions of an illustrative embodiment of apparatus in accordance with the invention.
Figure 32:
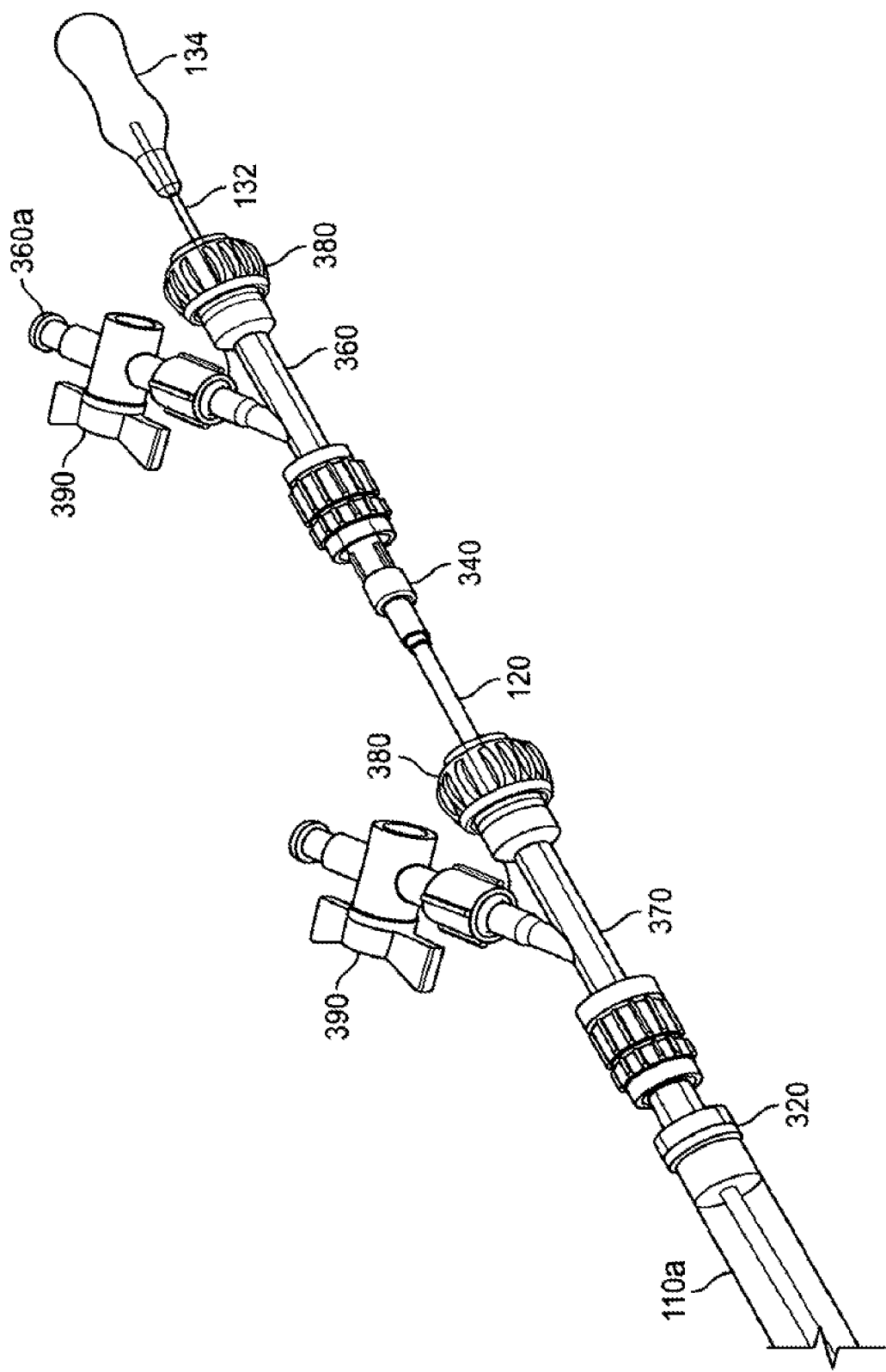
FIG. 32 is a simplified isometric or perspective view of other portions of an illustrative embodiment of apparatus in accordance with the invention.
Figure 33:
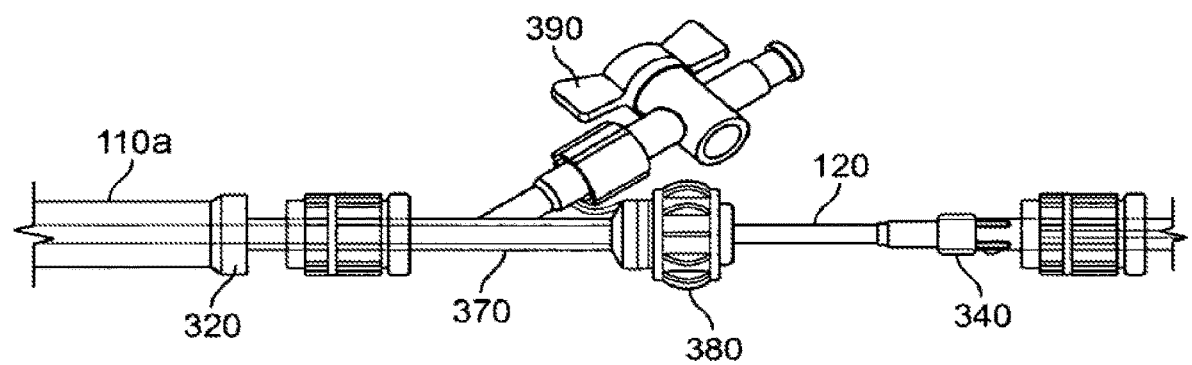
FIG. 33 is a simplified elevational view of portions of an illustrative embodiment of apparatus in accordance with the invention.
Figure 34:
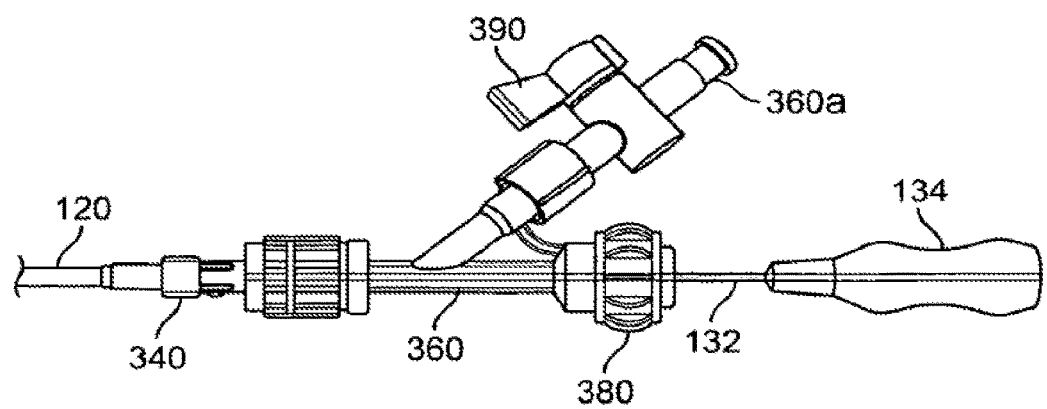
FIG. 34 is a simplified elevational view of other portions of an illustrative embodiment of apparatus in accordance with the invention.

The number of strands 210 and/or the pattern in which they attach to part 20c can differ from what is shown in FIGS. 28 and 29. For example, FIG. 30 shows the use of many more than three strands 210, and FIG. 30 also shows each strand having basically only one point of attachment to part 20c. Each such point of attachment is preferably radially out from the aperture (like 142) through which the associated strand 210 enters the lumen inside structures 120/140, and each point of attachment and the associated aperture (like 142) are on an associated radius that is preferably substantially perpendicular to the longitudinal axis of the delivery apparatus.

If, after valve 10 has been partly deployed in the patient, the location of the valve does not appear (e.g., fluoroscopically) to be as desired, the valve can be recollapsed back onto the delivery apparatus by pulling on the proximal ends of strands 210. The valve can then either be removed from the patient (by withdrawing the delivery apparatus from the patient), or the valve can be relocated in the patient (by manipulating the delivery apparatus to produce such relocation). Such valve removal or relocation may also include again closing the sheath structure(s) 110a and/or 110b around the outside of the valve. Assuming that valve relocation is the objective, when the valve is at the new location, it can be expanded again by releasing the tension on strands 210 and, if sheath 110a and/or 110b was re-closed around the valve, re-opening that sheath structure. When the valve is finally satisfactorily positioned in the patient, the valve can be finally released from the delivery apparatus by pulling one proximal end of each strand 210 proximally until the other end of the strand emerges out of the delivery system at the operator controlled end.

Although the above valve retrieval/repositioning structure is shown applied to valve part 20c, it will be understood that it can alternatively or additionally be applied to other valve parts such as 20a.

Strands 210 can be made of any suitable, sufficiently strong, sufficiently flexible, and sufficiently fine material and construction. Examples are wire (e.g., of nitinol), suture line, nylon line, or the like. The number and placement of the holes (like 142) for strands 210 to pass through the side wall of structure like 120/140 can be appropriate for the number and placement of the strands used.

The following is a description of an illustrative embodiment of the proximal (operator control, always outside the patient's body) portion of delivery apparatus 100, especially with reference to FIGS. 31-36.

Element 110a-b is again the main outer sheath of the delivery apparatus, with part 110a being the proximal sheath. This structure can facilitate introduction of fluids, which can be used to prep the delivery apparatus so that no gas (e.g., air) bubbles are introduced into the patient's circulatory system. Element 110a-b can also be used as a vessel that houses saline, which keeps valve 10 hydrated from the time it is loaded into the system until it is implanted in the patient. Structure 110a may also function as the proximal sheath, which controls/houses the crimped proximal end of the valve.

Component 320 is an end cap that (1) prevents fluid from leaking, (2) allows shaft 120 to pass through, and (3) allows connection to manifold 370.

Shaft or conduit 120 controls the crimped valve's axial movement for deployment and retrieval. Structure 120 facilitates introduction of fluids through port 360a, which aids in flushing and prepping the delivery apparatus.

Hub 340 is attached/integrated with shaft 120 and has a standard luer connection for connecting manifold 360.

Figure 35:
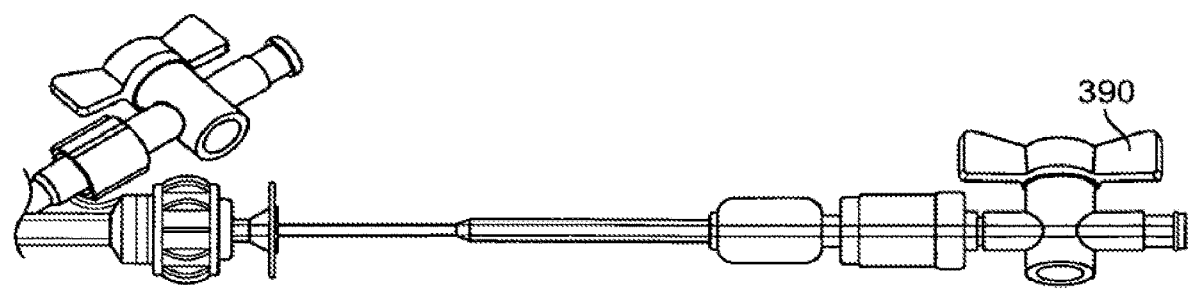
FIG. 35 is a simplified elevational view of portions of another illustrative embodiment of apparatus in accordance with the invention.
Figure 36:
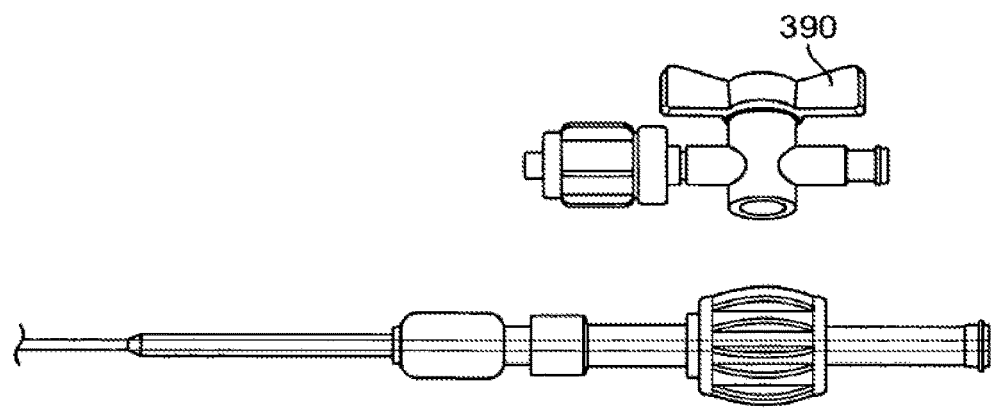
FIG. 36 is a simplified elevational view of several sub-assemblies from FIG. 35.

Inner lumen 132 may be a hypo-tube or any other conduit that is not limited to but allows introduction of ancillary devices such as guide wires, embolic protection devices, a balloon for pre-dilation of the implant site, fluids, etc. Also, shaft 132 is the means by which the distal sheath 110b is moved distally to release the distal end of the crimped valve. FIG. 35 shows an alternative having a valve connector 390 attached to the proximal end of inner lumen 132 (in lieu of molded handle 134 as in FIGS. 32-34). FIG. 36 shows another alternative in which manifold connectors 390, etc., can be attached to the proximal end of inner lumen 132 (again in lieu of molded handle 134). The FIG. 36 embodiment can provide a through port into the proximal end of inner lumen 132, whereby fluids and other devices of the types mentioned earlier (e.g., guide wires, embolic protection devices, balloons for pre-dilation of the implant site, etc.) can enter and pass through the entire length of the delivery apparatus (e.g., while delivery apparatus 100 is in place in the patient).

Manifold 360 functions as a fluid-tight valve control that forms a tight seal on shaft 132 when knob 380 (proximal occurrence) is turned clockwise. When locked (tightened), shaft 132 cannot be moved. Lever 390 (proximal occurrence) controls opening and closing of the fluid entry port into lumen 120. Fluids are introduced from this port, which has a standard luer for ancillary device attachment (e.g., syringes, etc.)

Manifold 370 functions as a fluid-tight valve control that forms a tight seal on shaft 120 when knob 380 (distal occurrence) is turned clockwise. When locked (tightened), shaft 120 cannot be moved. Lever 390 (distal occurrence) controls opening and closing the fluid entry port into lumen 110.

Knobs 380 (both occurrences) cause fluid to escape, but also allow free movement of the shafts passing through them. When these knobs are closed, they lock the associated shafts in place and prevent fluid leakage. They can be opened sufficiently to allow relative movement of the associated shafts without significant fluid leakage.

Valve levers 390 (both occurrences) can be opened to allow introduction of fluids. When closed, they prevent fluid introduction or leakage.

Although the foregoing tends to show valve 10 oriented in delivery apparatus 100 so that what will be the downstream portion 20c of the valve (in terms of blood flow through the valve after it has been implanted in a patient) is toward the distal end of the delivery apparatus, it will be understood that this orientation of the valve can be reversed if desired. The valve orientation that is generally shown herein is suitable, for example, for implanting an aortic valve via an antegrade approach (i.e., delivery apparatus 100 inserted in the blood flow direction). An example of such antegrade delivery is insertion of delivery apparatus 100 through an incision in the so-called apex of the heart (e.g., near the bottom of the left ventricle) and passage of the distal portion of delivery apparatus 100 up through the left ventricle until valve 10 is positioned adjacent the patient's native aortic valve annulus, where the valve can be deployed from the delivery apparatus and thereby implanted in the patient. (This may be referred to as a transapical approach.) A typical final disposition of the valve is with the extreme lower portion of valve frame part 20a flared out below and lodged against the native valve annulus, with the more distal portion of frame part 20a passing tightly through the native annulus, with struts 20b passing through the native valsalva sinus, and with valve frame part 20c lodged tightly in the native aorta downstream from the valsalva sinus.

Alternatively, however, and as noted above, the orientation of valve 10 in delivery apparatus can be reversed, and then the implant site can be approached in the retrograde direction (i.e., opposite the direction of blood flow). For example, the distal portion of the delivery apparatus can arrive at the implant site in the patient (e.g., the location of the native aortic valve) after passing through the patient's aorta. Access can be via an incision in the side wall of the aorta, or from a more remote location in the patient's circulatory system that leads to the aorta (so-called percutaneous or transluminal delivery). The ultimate, final disposition of valve 10 in the patient can be the same as was just described above. The delivery apparatus of this invention allows different portions of the valve to be released in whatever order is desired, which order may differ depending on whether the antegrade or retrograde approach is used.

Figure 37:
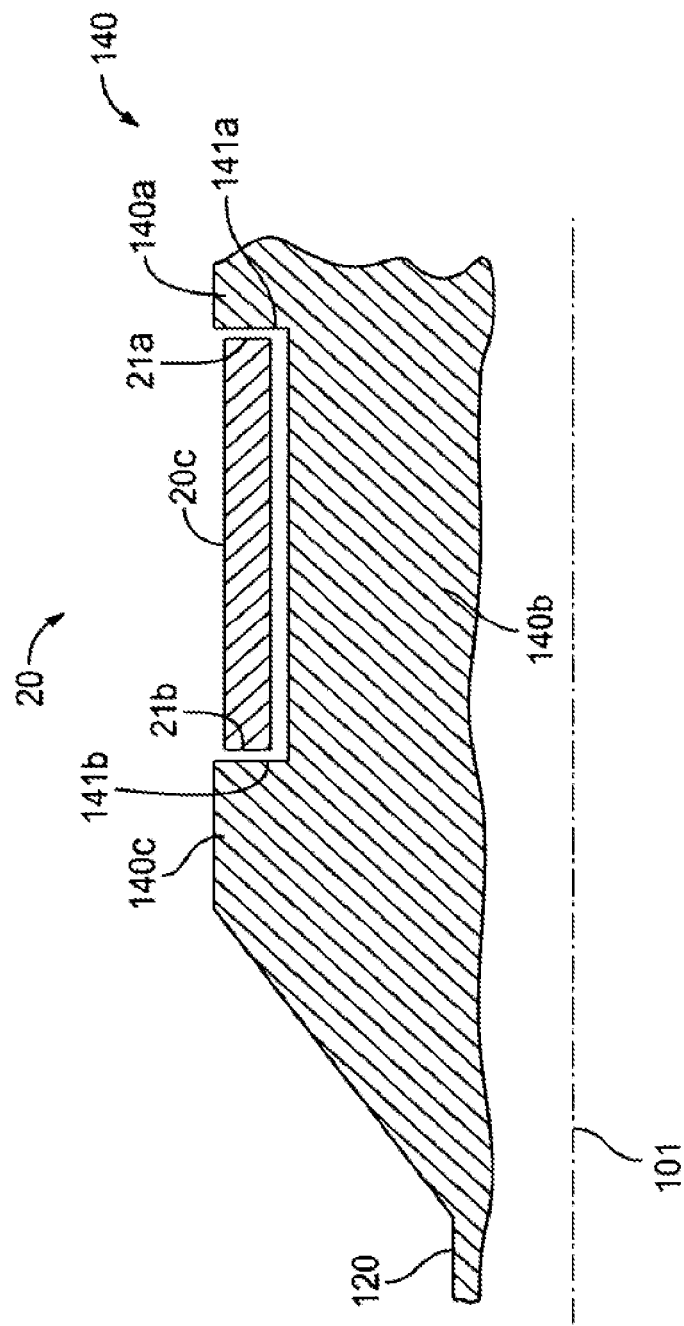
FIG. 37 is a simplified, partial, sectional view further illustrating certain possible aspects of the invention.

FIG. 37 illustrates in more detail a point made earlier regarding how valve support structure such as 140 can be constructed to cooperate with collapsed valve 10 to substantially prevent the collapsed valve from moving relative to the delivery apparatus parallel to the longitudinal axis of the valve and the delivery apparatus. FIG. 37 shows structure like that shown, for example, in FIGS. 1-10, 14, 16-18, 23, 24, 27, and 31. In particular, FIG. 37 shows a simplified, partial, sectional view of a distal portion of such structure. FIG. 37 shows that a distal portion 20c of the frame of collapsed valve 10 is disposed in a recess in the outer surface of the distal retainer 140 portion of the valve support structure of the delivery apparatus. For reference, a geometric longitudinal axis of valve 10 and delivery apparatus 100 is shown at 101. (FIG. 37 omits depiction of the sheath or sleeve structure 110 that may be present around the outside of what is shown in FIG. 37.)

The portion of valve frame 20 that is disposed in the above-mentioned recess in valve support structure 140 has first and second surface portions 21a and 21b that face in respective opposite first and second directions along axis 101. Valve support structure 140 (in particular the above-mentioned recess) has third and fourth surface portions 141a and 141b that respectively face in the second and first directions. The first and third surface portions 21a and 141a are positioned adjacent to and facing one another. Similarly, the second and fourth surface portions 21b and 141b are positioned adjacent to and facing one another. These relationships among surfaces 21a/b and 141a/b substantially prevent relative movement of valve 10 and valve support structure 140 along axis 101 while the valve is disposed around the valve support structure in the collapsed condition. For example, this secure holding of the valve means that the valve can be placed where desired in the patient, and then any sheath or sleeve structure like 110a/b can be moved relative to the valve and the valve support structure without disturbing the desired location of the valve in the patient. This may be especially important in cases in which the valve frame is resiliently biased to press outwardly against the surrounding sheath. Without secure positioning of the valve relative to its support structure, the valve might be dragged with the sheath when the sheath is shifted relative to the valve support. This could disturb the location of the valve in the patient and/or make it difficult to get the valve out of the sheath.

Figure 38:
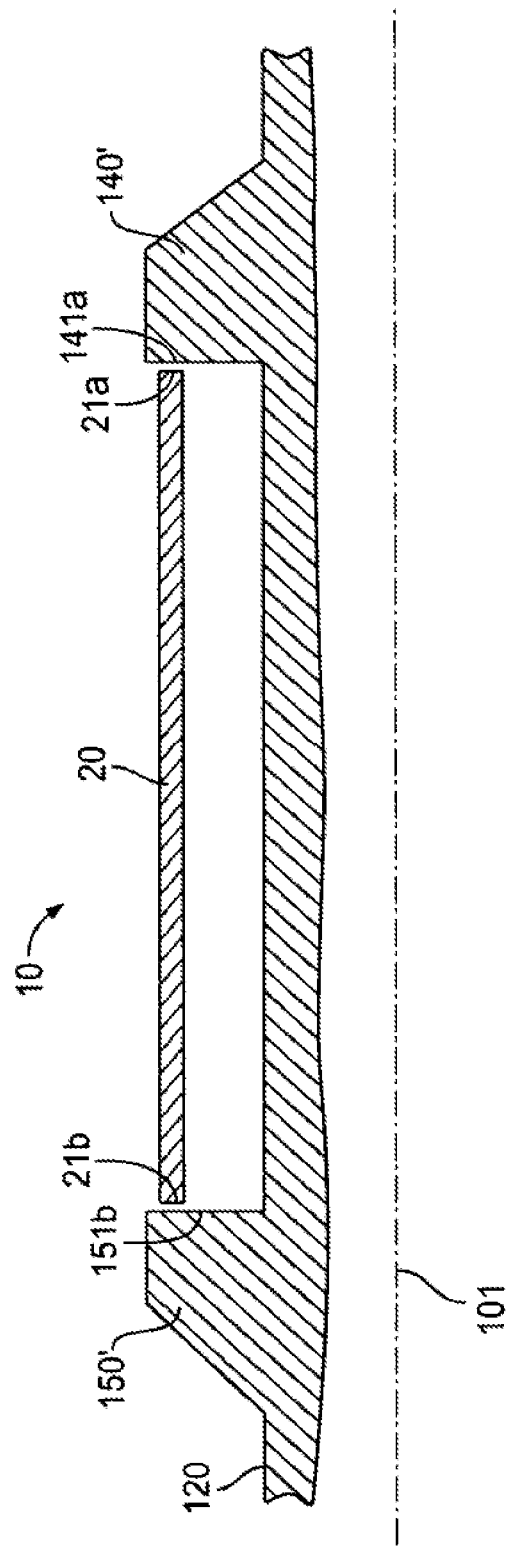
FIG. 38 is a another simplified, partial, sectional view further illustrating certain possible aspects of the invention.

FIG. 38 brings out the same point (made above in connection with FIG. 37) for embodiments like those shown in FIG. 15. Thus FIG. 38 shows that the frame 20 of valve 10 is received in a recess between the distal bumper 140' and the proximal bumper 150' of the valve support structure. Valve frame 20 has first and second surfaces 21a and 21b that face in respective opposite first and second directions along axis 101. Valve support structure 120/140'/150' has third and fourth surface portions 141a and 151b that respectively face in the second and first directions. The first and third surface portions 21a and 141a are positioned adjacent to and facing one another. Similarly, the second and fourth surface portions 21b and 151b are positioned adjacent to and facing one another. These relationships among surfaces 21a/b and 141a/151b substantially prevent relative movement of valve 10 and valve support structure 120/140'/150' along axis 101 while the valve is disposed around the valve support structure in the collapsed condition. For example, this secure holding of the valve means that the valve can be placed where desired in the patient, and then any sleeve structure like 110a/b can be moved relative to the valve and the valve support structure without disturbing the desired location of the valve in the patient.

Another way to describe possible features of the invention of the type highlighted by FIGS. 37 and 38 is to say that the valve support structure has elements that extend radially out at least into a tubular geometric shape in which the frame of the collapsed valve is disposed on the valve support structure. These elements are positioned to positively interfere with and thereby prevent relative axial movement of the collapsed valve and the valve support structure. Specific examples of such outwardly projecting elements on the valve support structure are the outer portions of elements 140a, 140c, 140', and 150'. These elements operate to hold the collapsed valve in a fixed axial position on the valve support structure of the delivery apparatus by contacting axially facing surfaces of the valve frame if the valve attempts to move axially relative to the support structure.

Figure 39:
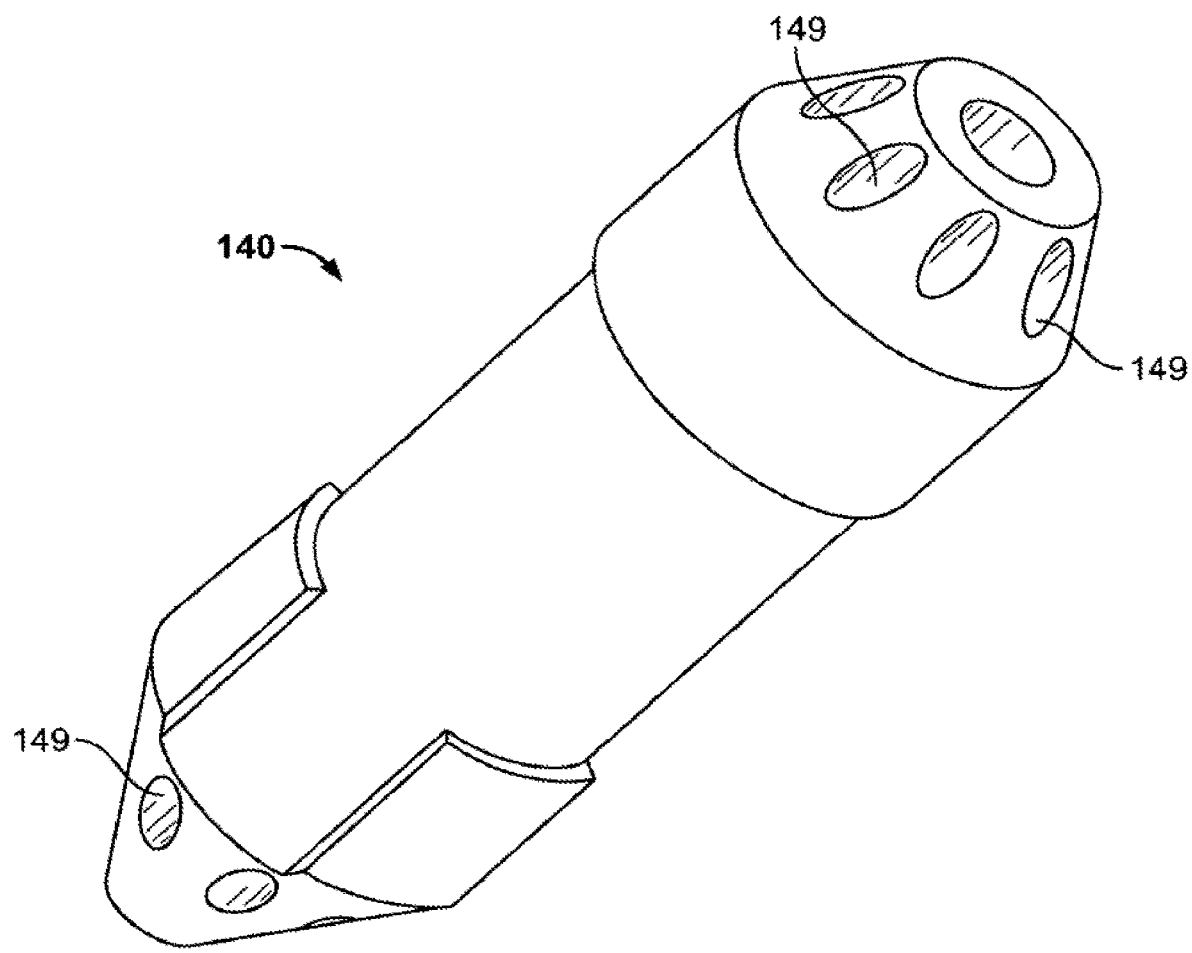
FIG. 39 is a simplified isometric or perspective view of an illustrative embodiment of a component that may be included in apparatus in accordance with the invention.
Figure 40:
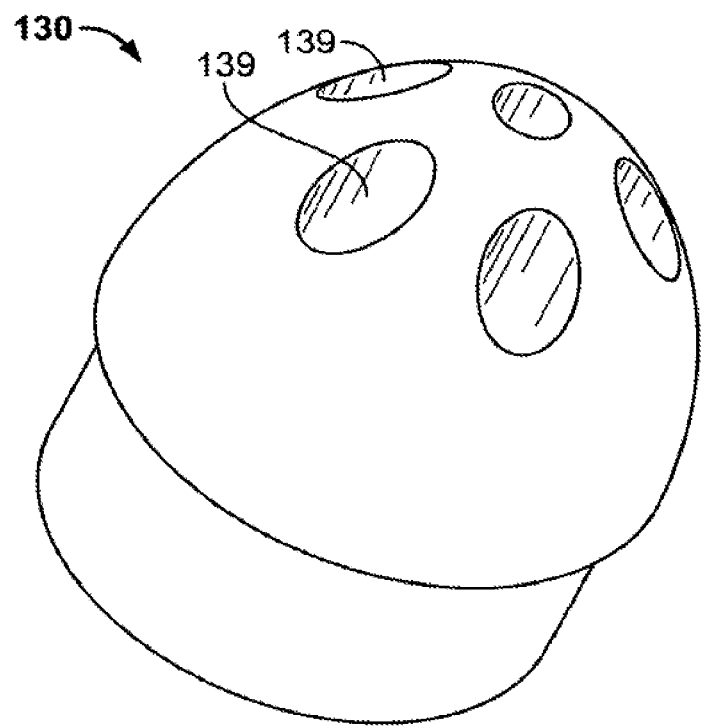
FIGS. 40 and 41 are simplified isometric or perspective views of an illustrative embodiment of another component that may be included in apparatus in accordance with the invention.
Figure 41:
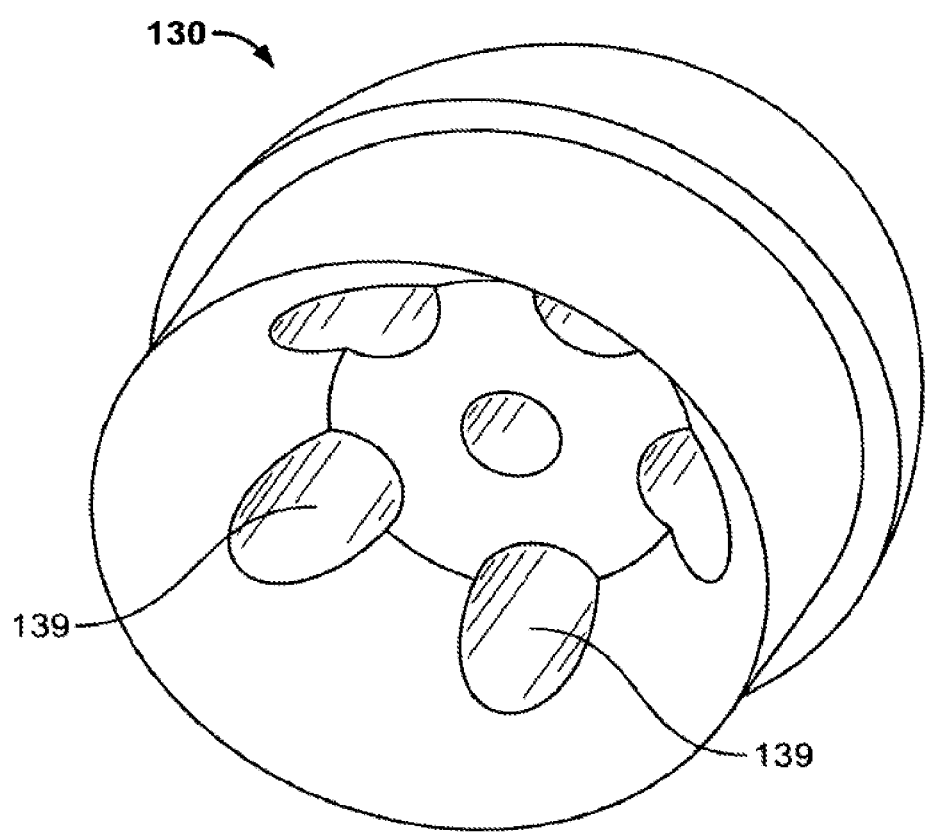

FIGS. 39-41 illustrate further possible features of the invention. These are holes 149 that extend longitudinally through valve support structure 140 and/or holes 139 that extend longitudinally through distal tip structure 130 and that can be used to facilitate de-airing of the apparatus prior to use. For example, the apparatus can be held vertically, with distal tip 130 up, during such de-airing. A saline solution can be introduced into the bottom of sheath 110 (e.g., via valve 390 or the like). As the saline level rises in the apparatus, air is forced out via vent holes 139. Holes 149 ensure that air and saline from below support 140 can pass that support and reach distal tip 130. When saline begins to flow out of vent holes 139, it is known that all of the air is out of the apparatus. (The interior of shaft 120 can be similarly de-aired by a parallel operation that includes introducing saline into the lower end of shaft 120 so that all air in that shaft also exits from the apparatus via vent apertures 139.)

Figure 42:
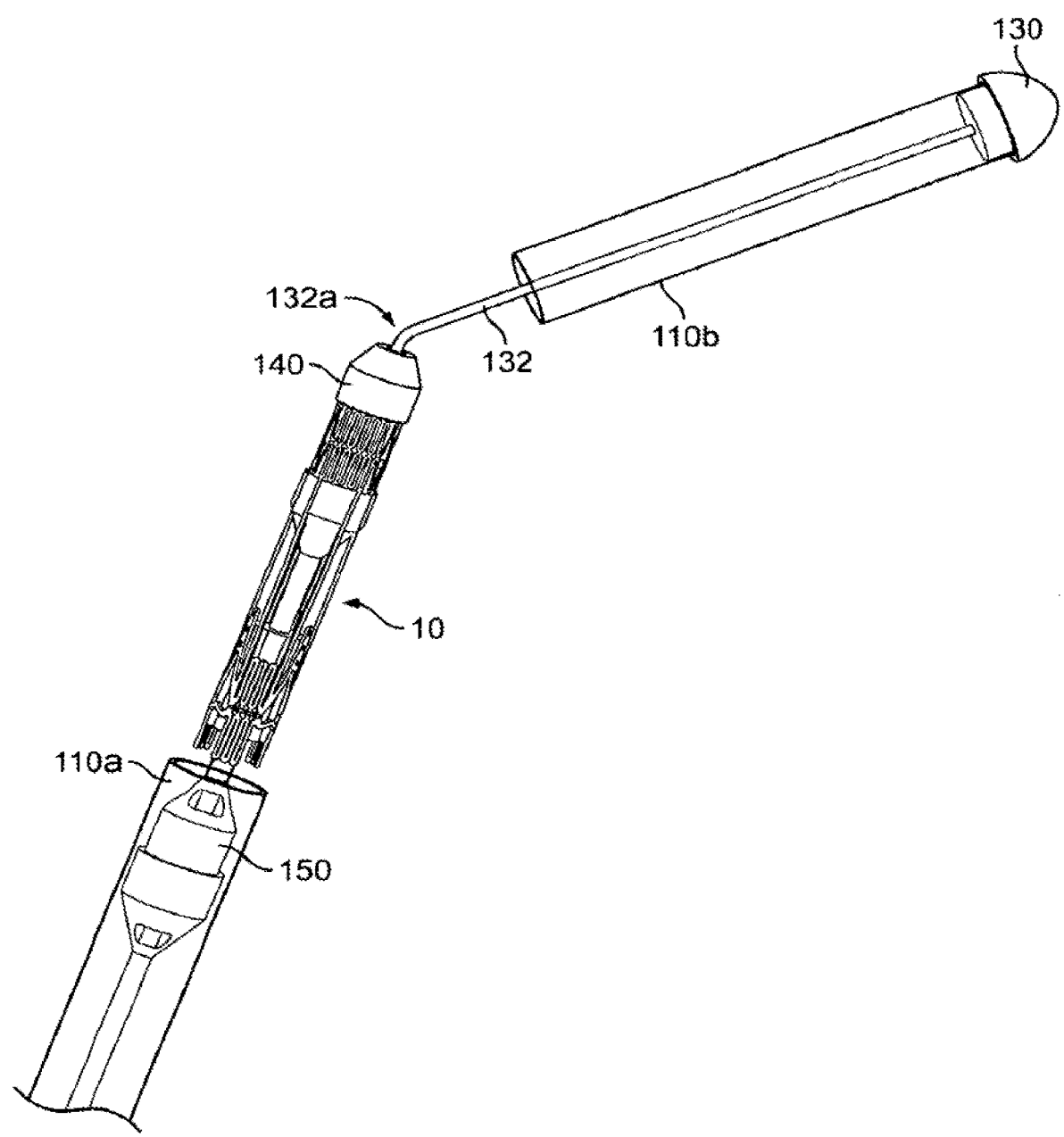
FIG. 42 is a simplified isometric or perspective view of an illustrative embodiment of apparatus in accordance with the invention and showing another possible feature of such apparatus.

FIG. 42 illustrates yet another possible feature in accordance with the invention. This is making shaft 132 so that it can articulate (bend relatively easily) in an articulation area or location 132a. This articulation location 132a is preferably somewhat proximal of the proximal end of sheath portion 110b. The purpose of this is to allow distal structures 130, 110b, and the portion of shaft 132 that is distally beyond articulation 132a to deflect laterally in order to somewhat follow the curvature of the patient's aortic arch when these elements are pushed distally into that arch to expose valve 10 for deployment in the vicinity of the patient's native aortic valve annulus, etc. This helps reduce resistance to distal motion of elements 130 etc. that might otherwise result from contact of the aortic arch by those elements.

The following recapitulates and extends various aspects of what has been said above.

This invention relates to a collapsible/expandable valve delivery system which can collapse, retain, maintain, transport, deploy, release, and help anchor a collapsible valve via a minimally invasive surgical port access or a percutaneous approach.

The system includes several components working together to facilitate access, delivery, deployment, expansion, and retrieval (if desired) of the collapsed valve. The delivery system has several elongated shafts and conduits that retain and facilitate precise deployment (among other functions) of the collapsed valve located at the distal end of the delivery apparatus. At the proximal end, several shafts/conduits slide over/relative to one another, which controls the advancement, deployment, fluid delivery, and recollapse of the valve. The valve is mounted onto the middle shaft utilizing specially designed retainers. The collapsed valve is retained in its collapsed condition via two tubular sheaths. The two sheaths collectively cover, contain, and protect the entire valve. The two sheaths move in a manner that gives the operator flexibility in deploying the valve's proximal or distal end first. Some embodiments use only one sheath.

The invention allows flexibility in implanting the replacement prosthetic valve using an antegrade or retrograde approach. The system has multiple lumens that connect manifold ports at the proximal end of the delivery apparatus to an opening or port at the distal end (tip). These lumens can be utilized for various functions such as delivery of fluids (temperature-controlled saline, contrast, etc.) and deployment of embolic protection devices, balloons for valvuloplasty, etc.

The delivery system can be manufactured from materials that are known to be biologically compatible for short-term human interaction, because the delivery device is not a permanent implant. Considerations to material selection are given because this device will come in contact with a permanent implant (prosthetic valve).

Manufacturing Steps: The delivery apparatus can be manufactured using a combination of extruded, injection molded, insert molded, machined, drawn surgical grade SS tubing, and other parts. The device components can fit together using various means of mechanical, thermal, or chemical bonding (interference fit, adhesion, welding, tabs, slots, heat bonding, etc.) to facilitate building a seamless working system.

Operational Steps: The delivery apparatus can be introduced from any of the previously described approaches. Once satisfactory axial and radial positioning are achieved, the deployment sequence begins. The valve can be deployed proximal-end-first or distal-end-first. In the aortic valve case (and depending on the valve's design and/or geometry), it is preferred to deploy the valve's proximal end first in order for it to flare out. In doing so, the delivery apparatus can be advanced forward slightly until resistance is felt. This tactile feedback to the operator is an indication that optimal axial alignment has been achieved as the valve's skirt is sub-annular of the native valve. While maintaining a slight pressure forward on the delivery apparatus to maintain the valve's axial position, the distal end can now be deployed by advancing the distal sheath forward. During proximal and/or distal end deployment, temperature-controlled saline can be infused to facilitate a slow, controlled deployment of a temperature-sensitive nitinol valve frame. This can prevent sudden "snap open" of the valve, which may be undesired because it may cause a dissection or other damage at the implant site. The saline temperature can be slowly increased to ultimately reach body temperature. This allows the valve to expand to its fully expanded and optimal geometry.

While the valve is partially or fully deployed but not fully released, it is possible to recapture it for repositioning or full retrieval if desired. Specially designed eyelets in the valve frame can facilitate the use of members made from appropriate materials such as thin nitinol wire, fish line, stainless steel wire, etc., which are attached in a manner that can control the recollapse of the valve. Once recollapsed, the valve can be repositioned or fully retrieved.

The delivery system is preferably designed around a durable and efficient valve design, thus not compromising any of the valve's long-term implant performance requirements. The delivery system preferably gives the operator the flexibility and freedom to control the deployment of the valve based on the chosen approach, patient anatomy, and disease state, among other important considerations. The system preferably offers several desirable features that make the valve easier to deliver and retrieve and accommodate supplemental and existing ancillary devices that may be used to successfully complete the procedure.

This delivery device design can be used in a femoral access, transapical access, transseptal access, or a direct small port access in the ascending aorta. With the preferred delivery system design, access to any of the heart's valves (aortic, mitral, pulmonary, and tricuspid) can be achieved for the purposes of repair and/or replacement of defective native valves.

The following is a recapitulation of various possible features of the invention.

Low-profile delivery system for collapsing, maintaining, delivering, deploying, repositioning, and retrieving (if desired) collapsible/expandable valves.

Delivery system can be fine-tuned to the delivery approach (retrograde or antegrade).

Radio-opaque markers can be placed in strategic areas and around the valve for guidance and visualization of valve and delivery system distal end under fluoroscopy or other visualization systems.

Capabilities in fully deploying the valve but not releasing it when repositioning or full recapture for retrieval is desired.

Delivery system with multi-lumen capabilities to facilitate procedural support by using ancillary devices such as guide wires, balloon catheters, embolic protection devices, fluids delivery (flushing or visualization), etc.

Several shafts/lumens moving relative to one another as follows: (1) Outer shaft: will sheath, collapse, and release valve; creates a conduit for flushing fluid around the valve. (2) Middle shaft: to advance and retract crimped valve relative to outer and inner shafts. (3) Inner shaft: to advance distal sheath for deployment of valve's distal end; also has a lumen to allow advancement over a wire, as well as a conduit for fluid delivery.

Valve is secured in place using sheaths and retainers. Retainers are mounted on the middle shaft and move with the valve. Sheaths move over the crimped valve.

Movable sheaths that function as valve retaining/collapsing mechanism. Also can maintain and protect the valve in the collapsed state. Create the outer edge of a conduit for fluids such as temperature-controlled saline.

A unique split sheath design (proximal and distal sheath halves). The distal half is attached to the tip, which is also attached to an elongated shaft that is controlled and actuated at the proximal end. Pushing this sheath distally deploys the distal end of the valve. The sheath other half is attached to the remainder of the delivery apparatus and moves proximally relative to the valve, which deploys the proximal end of the valve.

Features that control the valve's rotational (angular) orientation within the delivery system so it can be deployed with the correct radial orientation (e.g., to align with native valve commissures and avoid coronary artery obstruction).

Capability of opening and closing off access to any of the lumen ports back at the manifold connector.

Capability to lock the shafts of the delivery apparatus in position relative to one another, which also seals conduits, in addition locking in position.

Proximal valve retainer: (1) Centers the proximal sheath on the main delivery apparatus longitudinal axis. (2) Allows fluids passage during delivery apparatus preparation and during administration of temperature-controlled saline. (3) Tapered ends to prevent edge tripping/catching of advancing/retracting elements. (4) Can facilitate a resting place for the valve proximal end.

Distal valve retainer: (1) Holds and controls distal valve ring and portion of connecting struts. (2) Prevents axial movement of the valve until unsheathed for final release. (3) Geometry of retainer conforms to specific valve frame geometry, providing relief where needed. (4) Tapered ends to prevent edge tripping/catching of advancing/retracting elements. (5) Prevents valve jump during final release as deployment sequence commences.

Proximal and/or distal retainers can include holes to facilitate passage of recollapsing elements. The elements are attached to the proximal or distal portions of the valve (or both) and are used to recollapse the valve for repositioning or retrieval.

The proximal and distal sheath interface can be designed to seal and interlock.

Although not depicted, the delivery system can incorporate a feature that can extend outside the shaft at the distal end to force open the calcified native leaflets prior to valve deployment and release.

Various design variations are possible but only a few are included for illustration. See, for example, the alternate design where the proximal sheath fully encapsulates the distal sheath. This provides protection to the distal sheath, and at the same time provides two sheath ID sizes with further design variations. This allows the valve proximal end to have a collapsed diameter slightly larger than the distal end, which provides more room and thus less leaflet tissue compression. A possible additional benefit of the distal sheath inside the proximal sheath is smoother system withdrawal during an antegrade approach such as a transapical approach. Once the valve is released from the system, the proximal sheath can be advanced forward until it is past the leaflets. The delivery system distal sheath can then be retracted inside the proximal sheath and the entire system can be removed going back through the valve. Note that during withdrawal, the leaflets will only encounter a smooth, continuous, tube surface, as compared to a scenario involving trying to pull the distal sheath through the leaflets and inside of the proximal sheath before removing the entire system.

It will be understood that the foregoing is only illustrative of the principles of the invention, and that various modifications can be made by those skilled in the art without departing from the scope and spirit of the invention. For example, many details of the shapes shown for various components are only examples of how those details can be formed.

The invention claimed is:

1. Apparatus for delivering a collapsible and re-expandable prosthetic heart valve to an implant site in a patient, the prosthetic heart valve having a frame and a valve assembly supported by the frame, the apparatus comprising:

a valve support structure around which the prosthetic heart valve is adapted to be disposed in a collapsed condition, the valve support structure including a shaft extending in a longitudinal direction, a support body mounted on the shaft, and a valve-receiving compartment defined around the shaft, the support body having a proximal section, a distal section and an intermediate section between the proximal section and the distal section, the proximal section having a first surface projecting radially outward from an intersection with the intermediate section and facing the distal section and the distal section having a second surface projecting radially outward from an intersection with the intermediate section and facing the proximal section, the second surface extending continuously around a circumference of the valve support structure, the first surface and the second surface together defining a capture region on an exterior of the intermediate section such that a portion of the prosthetic heart valve is receivable in the capture region when the prosthetic heart valve is in the collapsed condition around the valve support structure to substantially prevent movement of the prosthetic heart valve in the longitudinal direction; and a sheath adapted to surround the prosthetic heart valve when the valve is in the collapsed condition around the prosthetic heart valve support structure.

2. The apparatus as claimed in claim 1, wherein the proximal section has a plurality of reduced-diameter regions arranged annularly in spaced apart relationship about an outer surface of the support body, each of the plurality of reduced-diameter regions being in axial communication with the intermediate section.

3. The apparatus as claimed in claim 1, wherein the support body includes a plurality of apertures extending therethrough in the longitudinal direction, the plurality of apertures providing fluid passageways that extend from the valve-receiving compartment to a location distal to the support body.

4. The apparatus as claimed in claim 1, wherein the support body includes a lumen extending in the longitudinal direction and a plurality of apertures extending radially from the lumen to an exterior of the intermediate section of the support body, the lumen and the apertures together defining passageways for threads for encircling the prosthetic heart valve when the portion of the prosthetic heart valve is received in the capture region.

5. The apparatus as claimed in claim 1, further comprising a valve retainer mounted on the shaft at a position spaced in the longitudinal direction from the support body so as to define a valve-receiving compartment between the support body and the valve retainer.

6. The apparatus a claimed in claim 5, wherein the valve retainer includes a plurality of apertures extending therethrough in the longitudinal direction, the plurality of apertures providing fluid passageways that extend from a location proximal of the valve retainer to the valve-receiving compartment.

7. The apparatus as claimed in claim 6, wherein the valve retainer has a proximal section with a first diameter and a distal section with a second diameter smaller than the first diameter.

8. The apparatus as claimed in claim 1, wherein the sheath is movable between a closed condition covering the valve-receiving compartment and an open condition uncovering the valve-receiving compartment.

9. The apparatus as claimed in claim 8, wherein the sheath includes a first sheath section that covers a first portion of the valve support structure in the closed condition and a second sheath section that covers a second portion of the valve support structure in the closed condition, the second sheath section being movable relative to the first sheath section to move the sheath from the closed condition toward the open condition.

10. Apparatus for delivering a collapsible and re-expandable prosthetic heart valve to an implant site in a patient, the prosthetic heart valve having a frame and a valve assembly supported by the frame, the apparatus comprising:

a valve support structure around which the prosthetic heart valve is adapted to be disposed in a collapsed condition, the valve support structure including a shaft extending in a longitudinal direction, a support body securely mounted on the shaft, and a valve retainer securely mounted on the shaft, the valve retainer being spaced from the support body in the longitudinal direction so as to define a valve-receiving compartment between the valve retainer and the support body, the support body having a first surface facing the valve retainer and the valve retainer having a first section with a first diameter and a second section with a second diameter less than the first diameter such that the first section provides a second surface facing the support body, the prosthetic heart valve being receivable between the first surface and the second surface when the prosthetic heart valve is in the collapsed condition around the valve support structure to substantially prevent movement of the prosthetic heart valve in the longitudinal direction; and a sheath adapted to surround the prosthetic heart valve when the prosthetic heart valve is in the collapsed condition around the valve support structure.

11. The apparatus as claimed in claim 10, wherein the valve retainer includes a first plurality of apertures extending therethrough in the longitudinal direction, the first plurality of apertures providing fluid passageways that extend from a location proximal of the valve retainer to the valve-receiving compartment.

12. The apparatus as claimed in claim 11, wherein the support body includes a second plurality of apertures extending therethrough in the longitudinal direction, the second plurality of apertures providing fluid passageways that extend from the valve-receiving compartment to a location distal to the support body.

13. The apparatus as claimed in claim 12, further comprising an atraumatic tip positioned distal to the support body, the atraumatic tip including a third plurality of apertures extending therethrough in the longitudinal direction.

14. The apparatus as claimed in claim 10, further comprising an atraumatic tip positioned distal to the support body, wherein the valve retainer includes a first plurality of apertures extending therethrough in the longitudinal direction, the support body includes a second plurality of apertures extending therethrough in the longitudinal direction, and the atraumatic tip includes a third plurality of apertures extending therethrough in the longitudinal direction, the first plurality of apertures providing fluid passageways that extend from a location proximal of the valve retainer to the valve-receiving compartment, the second plurality of apertures providing fluid passageways that extend from the valve-receiving compartment to a location distal to the support body, and the third plurality of apertures providing fluid passageways to an exterior of the apparatus.

15. The apparatus as claimed in claim 10, wherein the support body includes a lumen extending in the longitudinal direction and a plurality of apertures extending radially from the lumen to an exterior of the intermediate section of the support body, the lumen and the apertures together defining passageways for threads for encircling the prosthetic heart valve when the prosthetic heart valve is in the valve-receiving compartment.

16. The apparatus as claimed in claim 10, wherein the sheath is movable between a closed condition covering the valve-receiving compartment and an open condition uncovering the valve-receiving compartment.

17. The apparatus as claimed in claim 16, wherein the sheath includes a first sheath section that covers a first portion of the valve support structure in the closed condition and a second sheath section that covers a second portion of the valve support structure in the closed condition, the second sheath section being movable relative to the first sheath section to move the sheath from the closed condition toward the open condition.

* * * * *